United States Patent
Kuhn et al.

(10) Patent No.: US 9,126,049 B2
(45) Date of Patent: *Sep. 8, 2015

(54) SHOCK REDUCTION USING ABSOLUTE CALIBRATED TISSUE OXYGEN SATURATION AND TOTAL HEMOGLOBIN VOLUME FRACTION

(75) Inventors: Jonathan L. Kuhn, Ham Lake, MN (US); Can Cinbis, Shoreview, MN (US); David A. Anderson, Stanchfield, MN (US); James K. Carney, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 491 days.

This patent is subject to a terminal disclaimer.

(21) Appl. No.: 12/797,781

(22) Filed: Jun. 10, 2010

(65) Prior Publication Data

US 2010/0317946 A1 Dec. 16, 2010

Related U.S. Application Data

(60) Provisional application No. 61/185,831, filed on Jun. 10, 2009.

(51) Int. Cl.
*A61B 5/00* (2006.01)
*A61N 1/362* (2006.01)
(Continued)

(52) U.S. Cl.
CPC .......... *A61N 1/3622* (2013.01); *A61B 5/02028* (2013.01); *A61B 5/1459* (2013.01);
(Continued)

(58) Field of Classification Search
CPC ............................ A61B 5/0059; A61B 5/0084
USPC ....................................................... 600/324
See application file for complete search history.

(56) References Cited

U.S. PATENT DOCUMENTS

| 4,180,078 A | 12/1979 | Anderson |
| 4,202,339 A | 5/1980 | Wirtzfeld et al. |

(Continued)

FOREIGN PATENT DOCUMENTS

| EP | 760476 | 3/1997 |
| EP | 1764034 | 3/2007 |

(Continued)

OTHER PUBLICATIONS (PCT/US2010/038082) PCT Notification of Transmittal of the International Search Report and the Written Opinion of the International Searching Authority, Mailed Aug. 27, 2010. 10 pages.

(Continued)

*Primary Examiner* — Tse Chen
*Assistant Examiner* — Hien Nguyen
(74) *Attorney, Agent, or Firm* — Evans M. Mburu

(57) ABSTRACT

An implantable medical device for detecting and treating an arrhythmia includes an optical sensor adapted for positioning adjacent to a blood-perfused tissue volume. In one embodiment for controlling arrhythmia therapies delivered by the device, the optical sensor is controlled to emit light in response to detecting an arrhythmia, detect light scattered by the volume of blood perfused tissue including measuring an optical sensor output signal corresponding to the intensity of scattered light for at least four spaced-apart wavelengths, and compute a volume-independent measure of tissue oxygen saturation from the detected light. The hemodynamic status of the arrhythmia is detected in response to the measure of tissue oxygen saturation.

29 Claims, 11 Drawing Sheets

(51) Int. Cl.

| | | |
|---|---|---|
| *A61B 5/02* | (2006.01) | |
| *A61B 5/145* | (2006.01) | |
| *A61B 5/1459* | (2006.01) | |
| *A61N 1/365* | (2006.01) | |
| *A61N 1/39* | (2006.01) | |
| *A61B 5/0215* | (2006.01) | |
| *A61B 5/042* | (2006.01) | |
| *A61B 5/11* | (2006.01) | |

(52) U.S. Cl.
CPC ........ *A61B5/14542* (2013.01); *A61N 1/36557* (2013.01); *A61N 1/3956* (2013.01); *A61B 5/0215* (2013.01); *A61B 5/042* (2013.01); *A61B 5/1116* (2013.01)

(56) References Cited

U.S. PATENT DOCUMENTS

| | | | |
|---|---|---|---|
| 4,230,122 A | 10/1980 | Lubbers et al. | |
| 4,399,820 A | 8/1983 | Wirtzfeld et al. | |
| 4,467,807 A | 8/1984 | Bornzin | |
| 4,548,209 A | 10/1985 | Wielders et al. | |
| 4,567,892 A | 2/1986 | Piocchi et al. | |
| 4,750,495 A | 6/1988 | Moore et al. | |
| 4,967,748 A | 11/1990 | Cohen | |
| 5,007,423 A | 4/1991 | Branstetter et al. | |
| 5,163,427 A | 11/1992 | Keimel | |
| 5,176,137 A | 1/1993 | Erickson et al. | |
| 5,188,105 A | 2/1993 | Keimel | |
| 5,188,108 A | 2/1993 | Secker | |
| 5,193,535 A | 3/1993 | Bardy et al. | |
| 5,213,098 A | 5/1993 | Bennett | |
| 5,218,962 A | 6/1993 | Mannheimer et al. | |
| 5,227,181 A | 7/1993 | Knudsen | |
| 5,354,316 A | 10/1994 | Keimel | |
| 5,364,316 A | 11/1994 | Brambilla | |
| 5,385,143 A | 1/1995 | Aoyagi | |
| 5,398,680 A | 3/1995 | Polson et al. | |
| 5,431,172 A | 7/1995 | Hoegnelid et al. | |
| 5,464,434 A | 11/1995 | Alt | |
| 5,470,345 A | 11/1995 | Hassler et al. | |
| 5,531,714 A | 7/1996 | Dahn et al. | |
| 5,545,186 A | 8/1996 | Olson et al. | |
| 5,588,427 A | 12/1996 | Tien | |
| 5,593,431 A | 1/1997 | Sheldon | |
| 5,596,986 A | 1/1997 | Goldfarb | |
| 5,683,432 A | 11/1997 | Goedeke et al. | |
| 5,725,219 A | 3/1998 | Gilbert | |
| 5,752,519 A | 5/1998 | Benaron et al. | |
| 5,769,785 A | 6/1998 | Diab et al. | |
| 5,855,593 A | 1/1999 | Olson et al. | |
| 5,879,294 A * | 3/1999 | Anderson et al. | 600/310 |
| 5,902,326 A | 5/1999 | Lessar et al. | |
| 6,144,866 A | 11/2000 | Miesel et al. | |
| 6,198,952 B1 | 3/2001 | Miesel et al. | |
| 6,226,540 B1 | 5/2001 | Bernreuter | |
| 6,236,882 B1 | 5/2001 | Lee et al. | |
| 6,292,698 B1 | 9/2001 | Duffin et al. | |
| 6,377,840 B1 | 4/2002 | Gritsenko et al. | |
| 6,473,632 B1 | 10/2002 | Myers | |
| 6,481,899 B1 | 11/2002 | Quast et al. | |
| 6,487,343 B1 | 11/2002 | Lewandowski et al. | |
| 6,512,940 B1 | 1/2003 | Brabec et al. | |
| 6,522,915 B1 | 2/2003 | Ceballos et al. | |
| 6,587,703 B2 | 7/2003 | Cheng et al. | |
| 6,599,250 B2 | 7/2003 | Webb et al. | |
| 6,615,064 B1 | 9/2003 | Aldrich | |
| 6,622,046 B2 | 9/2003 | Fraley et al. | |
| 6,667,803 B1 | 12/2003 | Flessland et al. | |
| 6,682,135 B2 | 1/2004 | Zheng | |
| 6,738,667 B2 | 5/2004 | Deno et al. | |
| 6,839,583 B1 | 1/2005 | Lewandowski et al. | |
| 6,839,592 B2 | 1/2005 | Grandjean | |
| 6,850,787 B2 | 2/2005 | Weber et al. | |
| 6,892,006 B2 | 5/2005 | Lewandowski et al. | |
| 6,944,488 B2 | 9/2005 | Roberts | |
| 6,997,879 B1 | 2/2006 | Turcott | |
| 7,043,294 B1 | 5/2006 | Paris | |
| 7,096,064 B2 | 8/2006 | Deno et al. | |
| 7,127,278 B2 | 10/2006 | Melker et al. | |
| 7,164,948 B2 | 1/2007 | Struble et al. | |
| 7,165,893 B2 | 1/2007 | Schmitz | |
| 7,177,686 B1 | 2/2007 | Turcotte | |
| 7,239,385 B2 | 7/2007 | Schmitz et al. | |
| 7,239,901 B2 | 7/2007 | Gritsenko | |
| 7,277,757 B2 | 10/2007 | Casavant et al. | |
| 7,302,294 B2 | 11/2007 | Kamath et al. | |
| 7,809,441 B2 | 10/2010 | Kane et al. | |
| 7,991,448 B2 | 8/2011 | Edgar, Jr. et al. | |
| 8,038,626 B2 | 10/2011 | Cinbis et al. | |
| 8,055,321 B2 | 11/2011 | Bernreuter | |
| 8,090,432 B2 | 1/2012 | Cinbis et al. | |
| 8,165,662 B2 | 4/2012 | Cinbis et al. | |
| 2003/0004412 A1 | 1/2003 | Izatt et al. | |
| 2003/0065365 A1 | 4/2003 | Zhu et al. | |
| 2003/0144584 A1 | 7/2003 | Mendelson | |
| 2003/0187480 A1 | 10/2003 | KenKnight et al. | |
| 2003/0199956 A1 | 10/2003 | Struble | |
| 2004/0024297 A1 | 2/2004 | Chen et al. | |
| 2004/0220629 A1 | 11/2004 | Kamath et al. | |
| 2005/0119586 A1 | 6/2005 | Coyle et al. | |
| 2005/0148832 A1 | 7/2005 | Reghabi et al. | |
| 2005/0277818 A1 | 12/2005 | Myers | |
| 2006/0009685 A1 | 1/2006 | Finarov et al. | |
| 2006/0025827 A1 | 2/2006 | Hatlesad et al. | |
| 2006/0106293 A1* | 5/2006 | Fantini | 600/323 |
| 2006/0253007 A1 | 11/2006 | Cheng et al. | |
| 2007/0024946 A1* | 2/2007 | Panasyuk et al. | 359/253 |
| 2007/0203406 A1 | 8/2007 | Anderson et al. | |
| 2007/0239052 A1 | 10/2007 | Bhunia | |
| 2007/0239053 A1 | 10/2007 | Bhunia | |
| 2007/0239215 A1 | 10/2007 | Bhunia et al. | |
| 2007/0255148 A1 | 11/2007 | Bhunia | |
| 2008/0004513 A1 | 1/2008 | Walker et al. | |
| 2008/0015424 A1* | 1/2008 | Bernreuter | 600/323 |
| 2008/0103538 A1 | 5/2008 | Walker et al. | |
| 2008/0208011 A1 | 8/2008 | Shuler | |
| 2008/0208020 A1 | 8/2008 | Cinbis | |
| 2008/0208269 A1 | 8/2008 | Cinbis et al. | |
| 2008/0306390 A1 | 12/2008 | Cinbis | |
| 2010/0130840 A1 | 5/2010 | Isaacson | |
| 2010/0185252 A1 | 7/2010 | Bjorling et al. | |
| 2010/0292548 A1 | 11/2010 | Baker, Jr. et al. | |
| 2010/0292549 A1 | 11/2010 | Shuler | |
| 2010/0317943 A1 | 12/2010 | Kuhn et al. | |
| 2011/0066017 A1 | 3/2011 | Kuhn | |

FOREIGN PATENT DOCUMENTS

| | | |
|---|---|---|
| EP | 1955653 | 8/2008 |
| GB | 1419701 | 12/1975 |
| WO | 9825669 | 6/1998 |
| WO | 03077750 | 9/2003 |
| WO | 2004091719 | 10/2004 |
| WO | 2007012931 | 2/2007 |
| WO | 2008105698 | 9/2008 |
| WO | 2008118042 | 10/2008 |
| WO | 2008151263 | 12/2008 |

OTHER PUBLICATIONS

Myers, Dean E., Noninvasive Method for Measuring Local Hemoglobin Oxygen Saturation in Tissue Using Wide Gap Second Derivative Near-Infrared Spectroscopy, Journal of Biomedical Optics 10(3), 03417 (May/Jun. 2005).

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305.

St Jude Medical, ME 317: Design for Manufacturability, Implantable Pulse Generator Optical Sensing System, Jun. 1, 2004, 225 pages.

(56) References Cited

OTHER PUBLICATIONS

M.N. Ericson et al., Development of an Implantable Oximetry-Based Organ Perfusion Sensor, Proceeding of the 26th Annual International Conference of the IEEE EMBS, Sep. 1-5, 2004, pp. 2235-2238.

JR Wilson et al., Noninvasive Detection of Skeletal Muscle Underperfusion with Near-Infrared Spectroscopy ion Patients with Heart Failure; Circulation: Journal of the American Heart Association, 1989;80; pp. 1668-1674.

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305, Jul. 30, 2003.

* cited by examiner

SHOCK REDUCTION USING ABSOLUTE CALIBRATED TISSUE OXYGEN SATURATION AND TOTAL HEMOGLOBIN VOLUME FRACTION

RELATED PRIORITY APPLICATION

The present application claims priority and other benefits from U.S. Provisional Patent Application Ser. No. 61/185,831, filed Jun. 10, 2009, entitled "SHOCK REDUCTION USING ABSOLUTE CALIBRATED TISSUE OXYGEN SATURATION AND TOTAL HEMOGLOBIN VOLUME FRACTION", incorporated herein by reference in it's entirety.

REFERENCE TO RELATED APPLICATIONS

Cross-reference is hereby made to the commonly-assigned related U.S. Applications: U.S. patent application Ser. No. 12/797,744, U.S. patent application Ser. No. 12/797,770, and U.S. patent application Ser. No. 12/797,736, all entitled "DEVICE AND METHOD FOR MONITORING ABSOLUTE OXYGEN SATURATION AND TOTAL HEMOGLOBIN CONCENTRATION"; U.S. patent application Ser. No. 12/797,815, U.S. patent application Ser. No. 12/797,816, and U.S. patent application Ser. No. 12/797,823, all entitled "TISSUE OXYGENATION MONITORING IN HEART FAILURE" to Cinbis et al.; U.S. patent application Ser. No. 12/797,831, entitled "ACTIVE NOISE CANCELLATION IN AN OPTICAL SENSOR SIGNAL", to Kuhn et al.; U.S. patent application Ser. No. 12/797,793, entitled "SHOCK REDUCTION USING ABSOLUTE CALIBRATED TISSUE OXYGEN SATURATION AND TOTAL HEMOGLOBIN VOLUME FRACTION", to Kuhn et al.; and U.S. patent application Ser. No. 12/797,800, and U.S. patent application Ser. No. 12/797,811, both entitled "ABSOLUTE CALIBRATED TISSUE OXYGEN SATURATION AND TOTAL HEMOGLOBIN VOLUME FRACTION", to Kuhn et al., all of which are currently pending and are incorporated herein by reference in their entireties.

TECHNICAL FIELD

The disclosure relates generally to medical devices and, in particular, to an implantable medical device and associated method for controlling the delivery of cardioversion/defibrillation shocks.

BACKGROUND

Cardiac arrhythmias can be detected and treated by implantable cardioverter defibrillators (ICDs). ICDs typically monitor an intracardiac electrogram (EGM) signal to determine a patient's heart rhythm. When tachycardia or fibrillation are detected, electrical stimulation therapies are delivered, which may include pacing therapies and/or cardioversion/defibrillation shock therapies. The delivery of a shock therapy can be painful to the patient and uses considerable battery charge. As such, it is desirable to avoid delivering shock therapy when unnecessary, for example when the arrhythmia is not life-threatening and the patient is hemodynamically stable.

An uncalibrated, oxygen saturation index can be determined using an implantable optical sensor detecting two or three light wavelengths for monitoring patient hemodynamics. The uncalibrated oxygen saturation index can be used in detecting hemodynamically unstable arrhythmias. The influence of motion, optical path length, sensor location, confounding physiological events or conditions, and the relationship of an uncalibrated oxygen saturation index to the physiological status of the tissue, e.g. to actual tissue oxygenation, can result in a broad statistical distribution of the responses of the oxygen saturation index to both hemodynamically unstable arrhythmias and to normal sinus rhythm resulting in reduced specificity in differentiating between the two. A need remains for improved sensors and methods for discriminating between hemodynamically stable and unstable arrhythmias. Such discrimination may be used in controlling the delivery of shock therapies.

DETAILED DESCRIPTION

Figure 1:
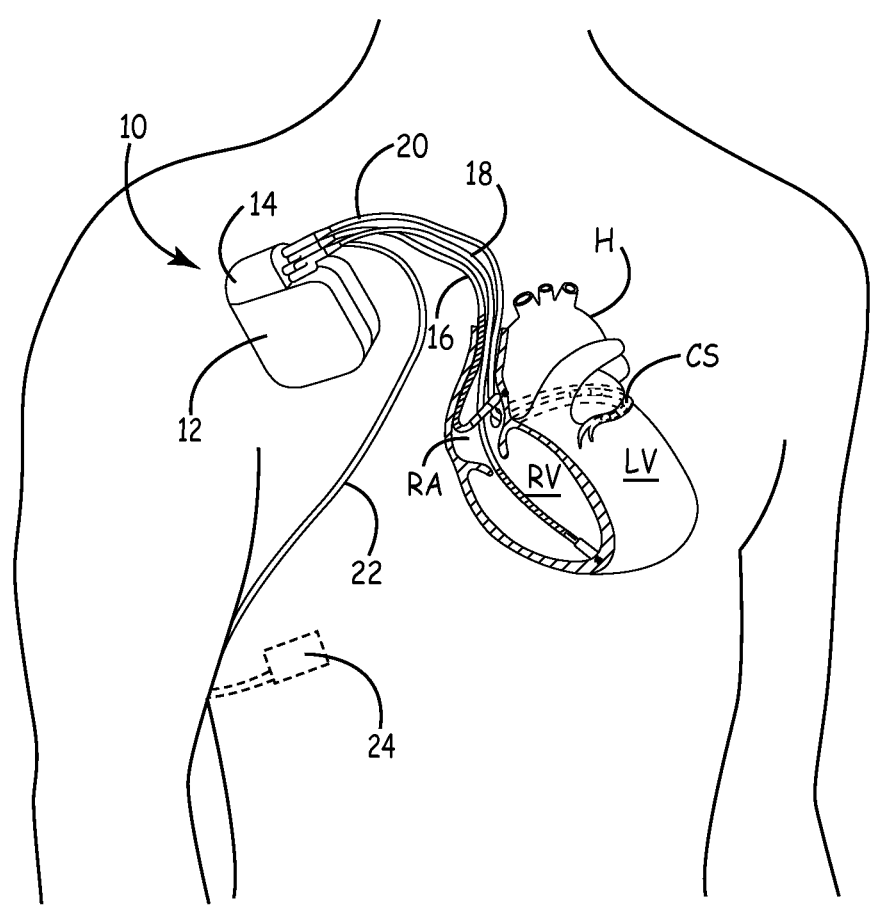
FIG. 1 is a schematic drawing of an implantable medical device (IMD) configured for both monitoring the function of and delivering therapy to a patient's heart.

In the following description, references are made to illustrative embodiments. It is understood that other embodiments may be utilized without departing from the scope of the disclosure. In certain instances, for purposes of clarity, the same reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In various embodiments described herein, an optical sensor is used to monitor tissue oxygenation in a measurement tissue volume. The measurement volume is the volume of tissue (including blood) in the optical path of the sensor. The term "tissue oxygenation" as used herein refers to the availability of oxygen to a localized tissue volume and thus refers to the availability of oxygenated hemoglobin. The term "total hemoglobin volume fraction" (HbT) refers to the concentration of red blood cells in a measurement volume carrying hemoglobin and thus relates to the total hemoglobin concentration as a fraction of a measurement volume. Stated differently, the total hemoglobin volume fraction, which can be expressed as a percentage, is the volume percentage of red blood cells carrying oxygenated and deoxygenated hemoglobin in the measurement volume. Thus a measurement of HbT will include contributions from red blood cells present in any arteries, capillaries, and veins which may be present in the measurement volume. Generally speaking, when the availability of oxygen to a body tissue is being monitored, the measurement volume of the optical sensor preferably extends through a uniform tissue volume such that optical sensor signals used to compute measurements of tissue oxygenation correlate to the absolute tissue oxygen saturation and HbT in the microcirculation of the measurement volume.

Absolute tissue oxygen saturation ($O_2$Sat) is the portion (or percentage) of the total hemoglobin that is in an oxygenated state. More specifically, $O_2$Sat relates to the available hemoglobin binding sites holding an oxygen molecule. Thus, "tissue oxygenation monitoring" as used herein refers to monitoring both $O_2$Sat (or an index thereof) and HbT (or an index thereof). Tissue oxygenation monitoring may involve determining absolute measurements of $O_2$Sat and HbT or determining trends of these measurements or trends of indices of these measurements.

Tissue oxygenation could be determined by a direct measurement of tissue oxygen partial pressure ($pO_2$). However, measurements of light scattering by blood chromophores allows measurement of $O_2$Sat and HbT in the microcirculation present in the measurement tissue volume to provide an indication of the availability of oxygen to the tissue. $O_2$Sat measured using an optical sensor as described herein is correlated to tissue oxygen partial pressure.

If the availability of oxygen is decreased due to any change in $O_2$Sat and/or HbT, tissue hypoxia may occur or already be present. As such, measurements of $O_2$Sat and HbT can be used to detect or predict tissue hypoxia without directly measuring the partial pressure of oxygen in the tissue. "Stagnant hypoxia" occurs when inadequate blood flow fails to transport sufficient oxygen to a blood-perfused tissue.

As used herein, "hemodynamic stability" refers generally to cardiac function that is adequate to maintain tissue oxygenation measurements acquired in a blood-perfused body tissue above a predefined threshold. "Hemodynamic instability" refers generally to cardiac function that is inadequate to maintain tissue oxygenation measurements above a predefined threshold. Hemodynamic stability may occur with compromised (reduced) but stable tissue perfusion and thus may be associated with stable (not decreasing) tissue oxygenation measurements even if the tissue oxygenation measurements are relatively lower than a normal tissue oxygenation level. Hemodynamic instability generally corresponds to tissue oxygenation measurements that continue to decrease toward an anoxic state associated with hemodynamic collapse.

FIG. 1 is a schematic drawing of an implantable medical device (IMD) 10 configured for both monitoring the function of and delivering therapy to heart H. In FIG. 1, heart H is shown in a partially cutaway view illustrating right atrium RA, right ventricle RV, left ventricle LV, and coronary sinus CS.

IMD 10 is shown embodied as an ICD that includes a pulse generator for delivering electrical stimulation to heart H for use in cardiac pacing therapies, cardioversion and/or defibrillation. Another example of an implantable medical device in which methods described herein may be practiced would be a subcutaneous cardioverter/defibrillator having electrodes implanted subcutaneously rather than transvenously as described here.

IMD 10 includes hermetically-sealed housing 12 and a connector block assembly 14 coupled to a right atrial (RA) lead 16, right ventricular (RV) lead 18, left ventricular (LV) lead 20, and optical sensor lead 22. IMD 10 further includes circuitry and a power source, which are located within housing 12, for controlling the operation of IMD 10. The circuitry communicates with leads 16, 18, 20, and 22 through electrical connectors within connector block assembly 14. A can electrode may be formed on or is a part of the outer surface of housing 12, and may act as an electrode in a unipolar combination with one or more of the electrodes carried by leads 16, 18 and 20.

Leads 16, 18, and 20 extend from connector block assembly 14 to right atrium RA, right ventricle RV, and coronary sinus CS adjacent left ventricle LV, respectively, of heart H. Leads 16, 18, and 20 each carry one or more EGM signals, attendant to the depolarization and repolarization of heart H, for providing pacing pulses for causing depolarization of cardiac tissue in the vicinity of the distal ends thereof, and for providing cardioversion/defibrillation shocks. When provided, a shock is typically delivered between a combination of electrodes carried on RA and RV leads 16 and 18 and the can electrode.

IMD 10 may include an optical sensor 26 along the housing 12 for emitting light into a tissue volume adjacent IMD 10 and detecting light scattered by the tissue volume for measuring light attenuation by the tissue. The measured light attenuation is used to compute tissue oxygenation measurements as will be described herein.

Alternatively or additionally, an optical sensor 24 may be carried by a lead 22 extending from IMD 10. Lead 22 extends from connector block assembly 14 to optical sensor 24, which is extravascularly-implanted, typically subcutaneously or submuscularly, at a desired tissue site. In other embodiments, sensor 24 may be carried by a lead and placed transvenously or transarterially in the blood stream itself. A lead-based sensor may be positioned to transmit light outward through the wall of a vessel to monitor oxygenation in adjacent tissue or to monitor oxygen saturation in the blood stream itself.

Sensor 24 may alternatively be embodied as a wireless sensor, implanted remotely from IMD 10 or worn externally by the patient. Sensor 24 provided as a wireless sensor includes telemetry circuitry for wireless telemetric communication with IMD 10. Various optical sensor configurations that may be implemented in conjunction with an ICD for use in controlling arrhythmia therapies are generally described in U.S. Pat. Application No. 61/185,824, hereby incorporated herein by reference in its entirety.

Figure 2:
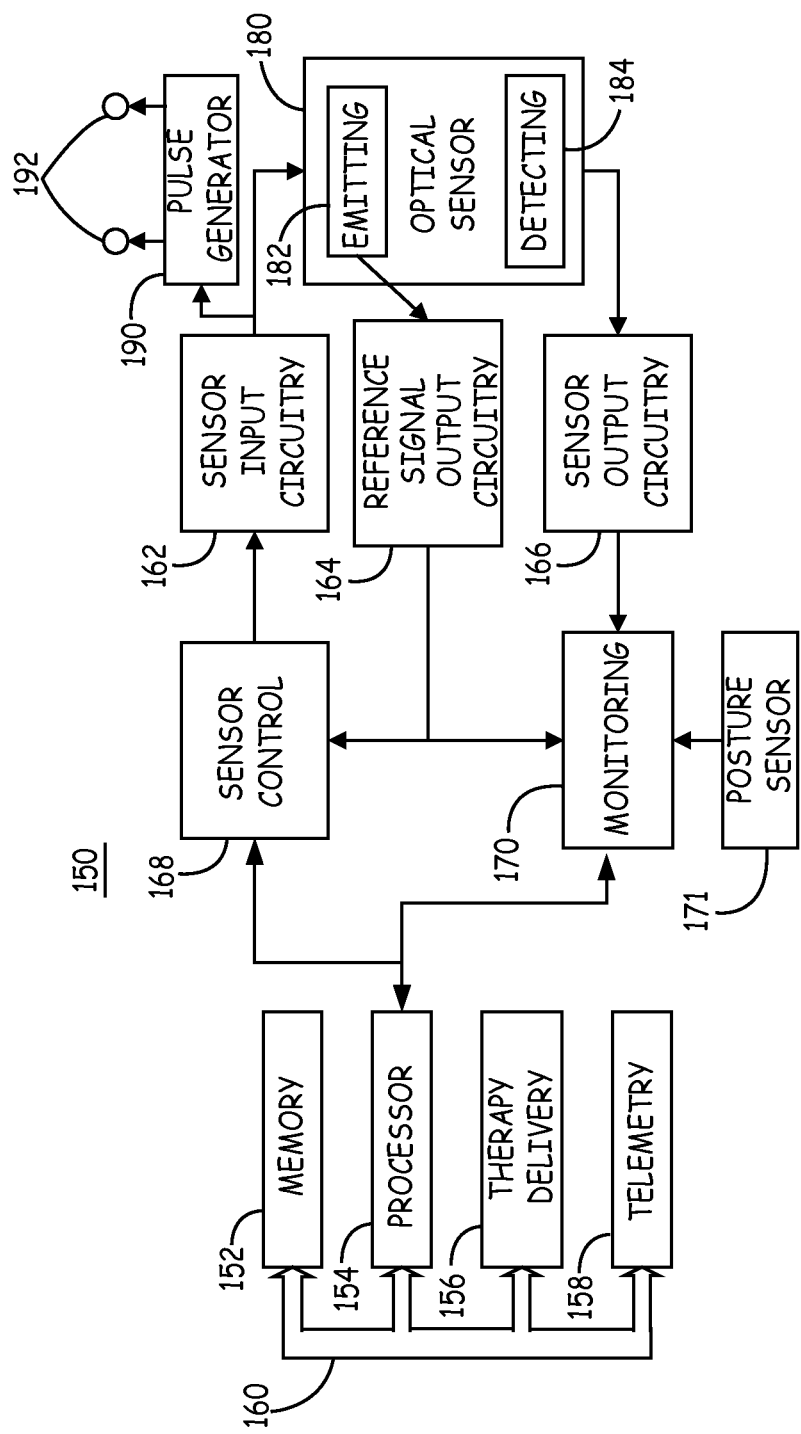
FIG. 2 is a functional block diagram of an IMD associated with an optical sensor for monitoring tissue oxygenation.

FIG. 2 is a functional block diagram of an IMD 150 associated with an optical sensor 180 for monitoring $O_2$Sat and HbT. IMD 150, which may correspond to the ICD shown in FIG. 1, includes (or is coupled to) an optical sensor 180, which may be incorporated in or on a hermitically sealed housing of IMD 150, carried by a lead extending from IMD 150, or embodied as a wireless sensor in telemetric communication with IMD 150. IMD 150 further includes sensor input circuitry 162, sensor output circuitry 166, and optionally includes reference signal output circuitry 164 when a reference photodiode is included in the optical sensor 180 for measuring the intensity of emitted light.

Optical sensor 180 generally includes a light source for emitting light through a blood perfused tissue of the patient and a light detector, also referred to herein as a "photodetector", for generating a signal representative of an intensity of light scattered by the blood perfused tissue to the light detector. The light passed through the tissue or bloodstream is selected to include four or more wavelengths for use in computing a volume-independent measure of O$_2$Sat, from which an absolute, calibrated O$_2$Sat may be derived. Typically, the intensity of scattered light falling in the red part of the visible light spectrum and the infrared (IR) portion of the light spectrum is measured. The light scattered by the blood perfused tissue and received by the light detector is generally correlated to the oxygenation of the tissue. Changes in tissue oxygenation may be caused by changes in hemodynamic function and may thus be used for discriminating between unstable and stable arrhythmias for use in controlling arrhythmia therapy delivery.

Sensor input circuitry 162 is coupled to a light emitting portion 182 of optical sensor 180. Light emitting portion 182 includes one or more light sources for emitting light that includes at least four different wavelengths. Light sources may emit light at discrete, spaced-apart wavelengths or a single white light source may be used. The measurement of scattered light for at least four different wavelengths allows a calibrated O$_2$Sat measurement to be obtained. Sensor input circuitry 162 provides input signals to the optical sensor 180. In particular, sensor input circuitry 162 provides the drive signals applied to the light sources included in light emitting portion 182 to cause controlled light emission, e.g. controlled intensity, time duration and frequency.

Sensor input circuitry 162 is controlled by sensor control module 168 which coordinates the beginning time, duration, and frequency of drive signals produced by sensor input circuitry 162. Control signals may include a period of no light emission for ambient light measurement. Drive signals may be applied to individual light sources simultaneously to cause "mixed" light emission from all light sources. In one embodiment, the drive signals are applied sequentially to cause sequential (i.e., non-simultaneous) light emission by individual light sources emitting light at spaced apart wavelengths. In this way, a light detecting portion 184 of sensor 180 will receive scattered light at an individual wavelength at any given time during the operation of sensor 180. It is recognized that referring to an "individual" or "one" wavelength can include a narrow bandwidth of wavelengths approximately centered on, or at least including, the specified individual wavelength emitted by a light source.

The sequential emission of light wavelengths allows multiple, scattered light signals to be sequentially measured for each wavelength. A single O$_2$Sat or HbT measurement will require some minimum interval of time corresponding to the cumulative time durations of each of the separately emitted wavelengths. The time-based sequencing of emitted light may include an interval of no light emission to allow for ambient light measurements and correction of the measured light signals for the presence of ambient light during light emission by the sensor.

In alternative embodiments, the sensor input circuitry 162 is controlled by sensor control module 168 to deliver drive signals simultaneously to each of the LEDs at separate, unique frequencies. Each LED will emit light having a signature frequency fluctuation. The detecting portion 184 will receive scattered light at all of the wavelengths corresponding to the LED wavelengths simultaneously with each wavelength modulated to a signature frequency. A photodetector signal is then demodulated to obtain the individual wavelength signals.

This frequency multiplexing method of controlling the light emitting portion 182 allows simultaneous light emission and detection such that changes in light attenuation by the tissue due to oxygen and hemoglobin changes in the measurement tissue volume can be measured simultaneously for all of the wavelengths rather than at discrete time intervals. This allows for a more instantaneous measurement of O$_2$Sat and HbT as compared to the sequentially-acquired signals for separate wavelengths in the time-multiplexed method of controlling light emission.

The different wavelengths may be modulated at frequencies that are much greater than the frequency of ambient light changes. Demodulation of the detected light signal will reduce or eliminate effects of ambient light artifact since the low frequency components of the detected light signal corresponding to ambient light changes will be substantially removed from the demodulated photodetector output signal.

Sensor output circuitry 166 receives the photodetector signal from light detecting portion 184 and demodulates and digitizes the signal to provide a digital signal to monitoring module 170. Sensor output circuitry 166 may include an analog-to-digital converter and memory for digitizing an analog output signal from detecting portion 184, providing the digitized signal to monitoring module 170, storing measurement results for future retrieval as well as storing calibration coefficients.

Monitoring module 170 uses the optical signal to compute a volume-independent measurement of O$_2$Sat and a measurement of HbT using the intensities of the multiple wavelengths measured by detecting portion 184. In some embodiments, a calibrated absolute O$_2$Sat and calibrated HbT are derived from the measurements and provided to a processor 154 (or other control circuitry) for detection and discrimination of arrhythmias.

In particular, the O$_2$Sat and HbT measurements may be used to detect a hemodynamically stable arrhythmia based on acceptable tissue oxygenation measurements obtained during an EGM—or other sensor-based arrhythmia detection. The detection of a hemodynamically stable arrhythmia could be used to delay a shock therapy. Delaying a shock therapy allows time for less aggressive arrhythmia therapies to be delivered, such as anti-tachycardia pacing therapies to be performed, time for the arrhythmia to spontaneously terminate, and/or time for additional arrhythmia detection and discrimination algorithms to be performed to correctly classify the arrhythmia and select the most appropriate therapy. The shock therapy may be avoided entirely for the detected arrhythmia episode if less aggressive therapies are successful or spontaneous termination occurs. Low or decreasing tissue oxygenation measurements obtained during arrhythmia detection may confirm the rhythm as a hemodynamically unstable arrhythmia, warranting delivery of a shock therapy.

As described above, IMD 150 is coupled to electrodes for use in sensing intracardiac EGM signals or subcutaneous ECG signals for detecting an arrhythmia. IMD 150 may include other sensors for sensing physiological signals such as blood pressure, patient activity, patient posture, temperature, or the like. Such sensor signals may be used in combination with the monitored O$_2$Sat and HbT for determining when a therapy is needed and delivered by therapy delivery module 156. Other sensor signals may be used to normalize, adjust or separate baseline and periodic tissue oxygenation measurements according to another monitored patient condition, such as local tissue temperature, sensor position changes due to changes in patient position, patient activity or the like.

For example, in one embodiment, a posture sensor 171 is included for use in detecting patient posture. Monitoring module 170 receives a signal from posture sensor 171 for use in detecting hemodynamically stable arrhythmias. Multiple tissue oxygenation thresholds may be defined for different patient postures. The posture sensor 171 may be embodied, for example, as a three-dimensional accelerometer and may be positioned in the same general location as the optical sensor 180. For example, if sensor 180 is included in an IMD housing that is implanted in a core body location, such as along the thorax, posture sensor 171 may also be included in the IMD housing to detect different patient postures such as standing, lying supine, side lying, and so forth. Alternatively, if optical sensor 180 is implanted along an extremity, such as the arm, a posture sensor may be implanted in the same general location or incorporated in optical sensor 180 to allow changes in arm position to be detected (e.g., arm raised or lowered).

Different thresholds based on patient position may be applied to tissue oxygenation measurements for detecting low tissue oxygenation associated with hemodynamic instability. As will be further described below, a posture sensor may also be used to control measurement of different baseline tissue oxygenation measurements to which a measurement during arrhythmia detection is compared.

Therapy delivery module 156 includes electrical pulse generation capabilities for delivering cardiac pacing pulses and cardioversion/defibrillation shocks. Therapy delivery module 156 may additionally include a fluid delivery pump for delivering a pharmaceutical or biological fluid to the patient and/or provide nerve stimulation therapy.

Data acquired by processor 154 relating to $O_2$Sat and HbT may be stored in memory 152 and/or transferred to a medical device programmer, home monitor, computer, or other external or bedside medical device via wireless telemetry module 158 for review by a clinician. Processor 154 transmits data to and from memory 152, therapy delivery module 156, and telemetry module 158 via data/address bus 160.

As will be described herein, some embodiments include a reference photodetector in the light emitting portion 182 of sensor 180. Reference signal output circuitry 164 may then be included for receiving a light detection signal from the reference photodetector and providing a reference output signal to sensor control 168 and/or to monitoring module 170. In one embodiment, the reference signal output circuitry provides an emitted light intensity feedback signal to sensor control 168 in a feedback control loop to maintain emitted light at each wavelength at desired relative intensities. Drive signals applied to a light source in light emitting portion 182 can be automatically adjusted to maintain the emitted light within a desired intensity range for each wavelength measured by the detecting portion 184. In this way, the emitted light spectra is reliably maintained over time promoting the accuracy of $O_2$Sat and HbT measurements computed using stored calibration constants or assuming stable light emission intensity. Accordingly sensor control 168 may include comparators, analog-to-digital convertors, and other logic circuitry for determining if a reference emitted light intensity signal is within a target range. If not within the desired range, the drive signal is adjusted by sensor control 168, e.g., in an iterative manner, until the target range is reached.

In an alternative embodiment, the reference emitted light intensity signal provided by circuitry 164 is received by monitoring module 170. Monitoring module 170 may use the emitted light intensity and a detected light intensity to compute light attenuation at each desired wavelength. The attenuation at each wavelength is used to compute second derivative attenuation spectra as will be described in greater detail below which enables derivation of a volume-independent measure of tissue oxygen saturation.

Alternatively, monitoring module 170 uses changes in the emitted light intensity to adjust a computed $O_2$Sat value. $O_2$Sat value may be computed assuming a stable emitted light intensity. The actual emitted light intensity may be measured and used to adjust a computed $O_2$Sat measurement. For example, an initially measured emitted signal intensity and a currently measured emitted signal intensity can be used to adjust or correct an absolute tissue oxygen saturation computed using only the photodetector signal from detecting portion 184 and calibration constants.

In some embodiments, IMD 150 includes electrodes 192 coupled to a pulse generator 190 (which may also be incorporated in therapy delivery module 156) for delivering electrical stimulation to excitable tissue adjacent to optical sensor 180. Electrical stimulation applied to the tissue volume that includes the optical pathway of sensor 180 may enhance detection of inadequate tissue oxygenation. Some methods for controlling arrhythmia therapy may include delivering electrical stimulation to the tissue adjacent optical sensor 180 when an arrhythmia is detected from sensed EGM/ECG signals. By increasing the metabolic demand of the local tissue, a faster decline in tissue oxygenation will be observed during hemodynamically unstable arrhythmia than during a hemodynamically stable arrhythmia. Likewise, a quicker recovery of tissue oxygenation will be observed upon terminating tissue stimulation when an arrhythmia is hemodynamically stable as compared to a hemodynamically unstable arrhythmia.

Figure 3:
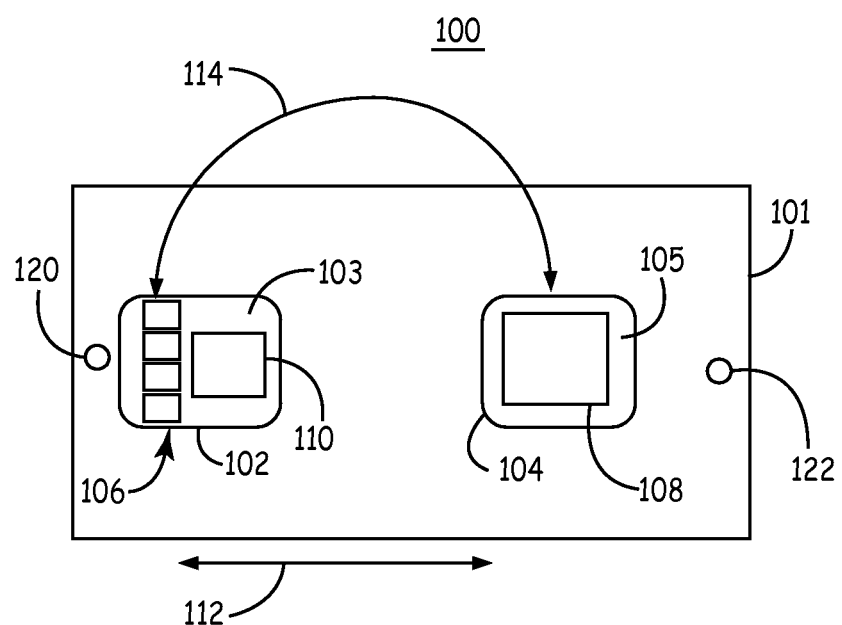
FIG. 3 is a top, schematic view of an optical sensor according to one embodiment.

FIG. 3 is a top, schematic view of an optical sensor according to one embodiment. It is recognized that numerous sensor configurations may be used for controlling arrhythmia therapy delivery, and the methods for monitoring tissue oxygenation for using in controlling arrhythmia therapy as described herein are not limited to any particular sensor configuration. In general, any optical sensor that acquires the scattered light intensity measurements required to compute a volume-independent measurement of $O_2$Sat may be used. Examples of other optical sensors that may be employed are generally described in U.S. patent application Ser. No. 12/797,744, hereby incorporated herein by reference in its entirety.

The sensor 100 shown in FIG. 3 includes a light emitting portion 102 and a light detecting portion 104. Light emitting portion 102 includes one or more light sources 106 positioned to emit light through a lens 103 sealed in an opening in hermetically-sealed housing 101. Light sources 106 may be embodied as single white light source or multiple light sources emitting light at separate spaced-apart wavelengths. In one embodiment, light sources 106 are embodied as light emitting diodes (LEDs) emitting light in the visible (e.g., red) and/or infrared light spectrum. Suitable light sources include, without limitation, optoelectronic devices such as LEDs, lasers such as vertical cavity surface emitting lasers (VCSELs), luminescent, phosphorescent or incandescent light sources.

For example, four LEDs are shown which may emit light at separate wavelengths of 680 nm, 720 nm, 760 nm, and 800 nm. Alternatively, the four LEDs provided as light sources 106 may emit light at 660 nm, 720 nm, 760 nm, and 810 nm. In another embodiment, four LEDs are included emitting light at 720 nm, 760 nm, 810 nm, and 850 nm. In yet another embodiment, four LEDs are included that emit light at 720 nm, 760 nm, 810 nm, and 890 nm. Any combination of LEDs emitting light at any of the wavelengths mentioned herein may be used. Furthermore, it is recognized that the specified wavelengths are approximate and each LED may emit a narrow band of light wavelengths which is approximately centered on, or at least includes, the specified wavelength.

In the embodiment shown, the light emitting portion 102 further includes a reference light detector 110, which may be embodied, for example, as a photodiode. The light entering an adjacent tissue volume from emitting portion 102 may change over time during chronic use of sensor 100 due, for example, to drift in the photonic output of light source(s) 106 and/or changes in the optical properties of the materials encountered by light emitted by light sources 106 before entering an adjacent tissue volume. Reference light detector 110 provides an output signal for measuring or detecting changes in the intensity of the light emitted by emitting portion 102.

The reference light detector 110 output signal can be used in computing or adjusting $O_2$Sat and HbT measurements as described above in conjunction with FIG. 2. Additionally or alternatively, an output signal from reference light detector 110 can be used as feedback signal for controlling the drive signals applied to light sources 106 to cause light emission.

In other embodiments, a light detector is not included in the emitting portion. The emitted light intensity is assumed to be stable throughout the usable life of the sensor so as not to introduce significant error in attenuation measurements.

The light detecting portion 104 includes a light detector 108 positioned to receive light through a lens 105 mounted in an opening in housing 101. The light detector 108 may be embodied as a photodiode and receives light scattered by an adjacent tissue volume. Other components suitable for use as a light detector include a photoresistor, phototransistor, photovoltaic cell, photomultiplier tube, bolometer, charge-coupled device (CCD) or an LED reverse-biased to function as a photodiode. The distance 112 between the light sources 106 and the light detector 108 will influence the optical path length 114, shown schematically. Greater spacing (longer distance 112) between the emitting and detecting portions will result in a longer optical path extending deeper in the adjacent tissue volume than relatively shorter distances.

In some embodiments, sensor 100 includes electrodes 120 and 122 for delivering local electrical stimulation to excitable tissue (e.g. skeletal muscle) adjacent to sensor 100. Local stimulation may be applied as one or more trains of pulses exceeding the stimulation threshold of the excitable tissue. The train of pulses may be delivered at a frequency high enough to cause a fused, tetanic contraction of skeletal muscle tissue. The duration and/or number of pulse trains may be fixed or variable. A variable pulse train duration or pulse train number may be terminated when tissue $O_2$Sat reaches some predetermined minimum or upon reaching a maximum cumulative pulse train duration, whichever comes first. For detecting hemodynamic stability, the total time the tissue is stimulated is expected to be limited to some maximum duration since arrhythmia discrimination is desirable within up to, for example, approximately 10 seconds in order to enable a quick response of the ICD to the arrhythmia.

Local stimulation of the tissue volume that includes the optical pathway 114 will increase the oxygen consumption of the tissue, which will be reflected as a decrease in tissue oxygenation measurements. This increase in metabolic demand will accelerate a decline in tissue $O_2$Sat when the patient is experiencing a hemodynamically unstable arrhythmia. By accelerating the decline in $O_2$Sat, a quicker discrimination of hemodynamically unstable and hemodynamically stable arrhythmias may be possible, thereby shortening the response time of the ICD.

Figure 4:
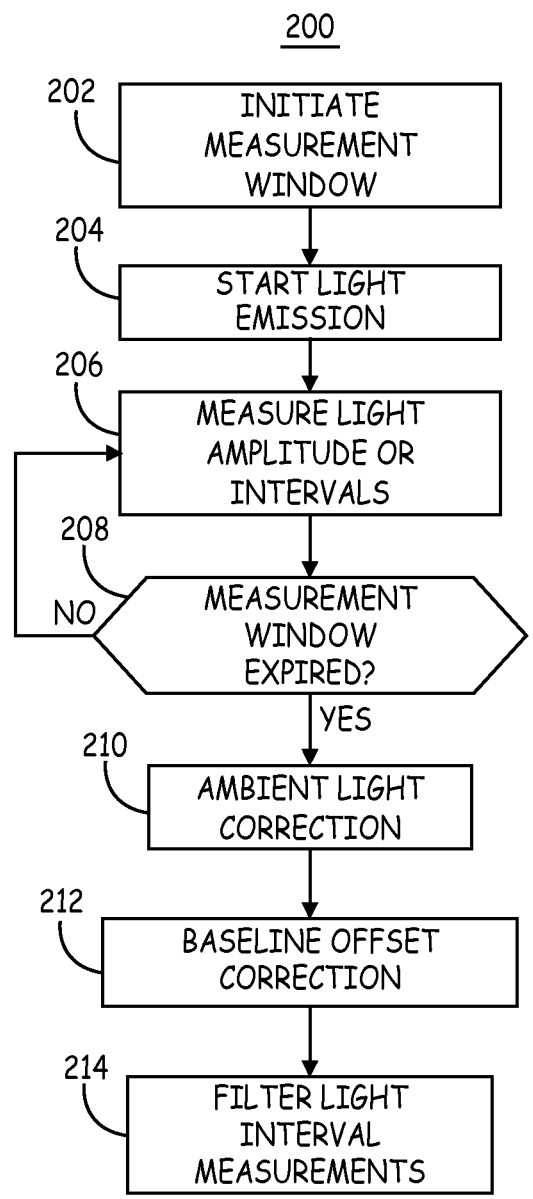
FIG. 4 is a flow chart of a method for operating an optical sensor to obtain photodetector output signals during tissue oxygenation monitoring.

FIG. 4 is a flow chart of a method 200 for operating an optical sensor to obtain photodetector output signals during tissue oxygenation monitoring. Flow chart 200 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a measurement time window is initiated. In various applications, tissue oxygenation monitoring may be continuous, periodic, or triggered in response to detecting physiological events monitored by the medical device, such as detecting arrhythmias,. In the example shown in method 200, tissue oxygenation monitoring is performed during a periodic or triggered measurement window. After initiating the measurement window, light emission is started at block 204. Light emission at selected wavelengths may be controlled in a time multiplexed or frequency multiplexed manner or provided as pulsed or continuous white or mixed light emission.

At block 206, the electrical output signal generated by the photodetector is measured. The output signal may be analyzed using an amplitude approach or an integration approach. In the integration approach, an integrator is included in the sensor output circuitry for integrating the photodetector signal, for example using a capacitor. The signal may be integrated over fixed time intervals, which may be on the order of approximately 0.10 to 100 ms for example. The magnitude of the integrated signal at the end of the fixed time interval is stored as a sample data point and corresponds to scattered light received by the light detecting portion of the optical sensor during the fixed time interval. Alternatively, the photodetector signal may be integrated until a predetermined integrated signal magnitude is reached and the time interval required to reach the predetermined magnitude is stored as a sample data point.

In other embodiments, the amplitude of the photodetector signal may be monitored directly by sampling the signal amplitude throughout the measurement window. Such sampling may correspond to pulsed light source activation, sequential time intervals of light source activation times during time multiplexed light source operation. Alternatively the frequency may be selected to be greater than the greatest frequency modulation of an light source in the emitting portion to allow sampling all of frequencies of emitted light in a frequency multiplexed algorithm.

The measurement window may be set to allow time to acquire a desired number of output signal sample points for each of the desired wavelengths. The photodetector signal amplitude or integrated signal amplitude or time interval continues to be sampled during the measurement window until it expires as determined at decision step 208. Depending on whether the measurement window is initiated as a periodic monitoring window or a triggered monitoring window, the duration of the measurement window may vary from a few seconds to a few minutes or longer.

After acquiring the desired number of samples, the drive signals controlling the light emitting portion may be turned off. Sampled data points may be stored and processed for computing O₂Sat and HbT as will be described further below. The sampled data points may be filtered or averaged at block 214 to provide smoothing of signal data or removal of artifact.

At blocks 210 and 212 corrections of sample data may be made to reduce the influence of ambient light and baseline offset. Corrections performed in blocks 210 and 212 may be executed before or after filtering at block 214. Ambient light may be measured directly by measuring the optical signal when the light emitting portion of the optical sensor is not emitting light. The ambient light contribution may then be subtracted from the light signal. Baseline offset (sometimes referred to as the "dark signal" or "dark interval") is caused by current leakage within the optical sensor electronics that occurs in the absence of light. Correction for the baseline offset for a given sensor can be made based on a dark signal or dark interval for that sensor, measured, for example, at the time of device manufacture and qualification testing. If the baseline offset exceeds a desired threshold, offset correction may be included at block 212 to subtract the offset from the incoming signal data. The resulting filtered, corrected sampled signal for each of the wavelengths of interest can be processed as will be further described herein for obtaining a volume-independent measurement of O₂Sat and a measurement of HbT for assessing oxygenation of the adjacent tissue volume.

Figure 5:
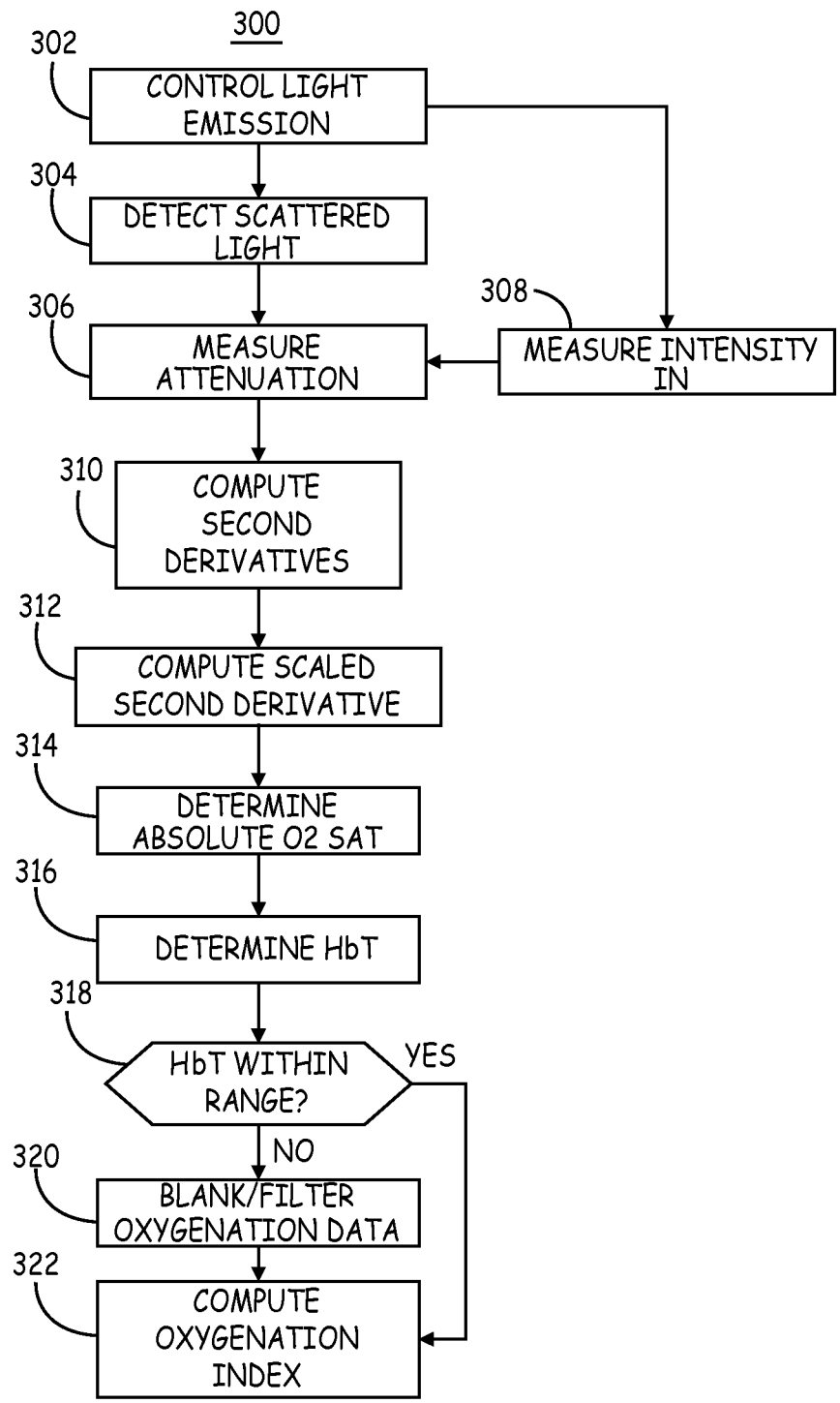
FIG. 5 is a flow chart of a method for operating an optical sensor during tissue oxygenation monitoring.

FIG. 5 is a flow chart of a method 300 for operating an optical sensor during tissue oxygenation monitoring. Method 300 generally corresponds to sensor operation after implantation as will be described in conjunction with FIG. 7. Once the sensor is calibrated and acceptably positioned, it is enabled for monitoring tissue oxygenation according to a programmed monitoring algorithm. For example, method 300 generally corresponds to operations performed during a measurement window set on a periodic or triggered basis as described above in conjunction with FIG. 4. The measurement window may also be set as a test measurement window during sensor implantation and calibration procedures.

At block 302, the light emitting portion of the sensor is controlled to emit light by applying drive signals to the light source(s). As described previously, light sources may be controlled to emit light at different wavelengths in a sequential, time-multiplexed manner or in a simultaneous frequency-multiplexed manner or at multiple simultaneous or mixed wavelengths when filtered in the detecting portion. A reference photodetector included in the light emitting portion provides an output signal for measuring the intensity emitted by the sensor at block 308. The output signal is demodulated or otherwise processed to provide an intensity of light emitted for each of the selected wavelengths at which attenuation will be measured.

At block 304, the emitted light scattered by the tissue volume is detected by the photodetector in the light detecting portion. The detecting portion provides an output signal corresponding to the intensity of light received. The output signal is demodulated or otherwise processed to provide an intensity of light received for each of the selected wavelengths.

At block 306, the attenuation spectrum is measured. In one embodiment, the attenuation of four wavelengths in the red to infrared spectrum is measured. The attenuation of the four different wavelengths may be measured using sequential detection of the different wavelengths by the photodetector when a time multiplexed light emission control algorithm is used. Alternatively, measurement of the four different wavelengths may involve demodulation of simultaneously detected light at the four different wavelengths when a frequency multiplexed light emission control algorithm is used. In other embodiments, remitted light from a white light source or simultaneously emitting single wavelength sources may be filtered to obtain the four different wavelength attenuation signals. In still other embodiments, LEDs configured for narrow-band light detection may be used to detect the four separate wavelengths.

The attenuation for a given wavelength (λ) can be measured as the negative logarithm of the ratio of the emitted light intensity ($i_{in}$) to the remitted light intensity ($i_{out}$):

$$A(\lambda) = -\log(i_{in}/i_{out})_\lambda \quad [1]$$

wherein $i_{in}$ can be measured using a reference photodetector in the light emitting portion of the sensor and $i_{out}$ is measured using the output signal of the light detecting portion for a given wavelength. Remitted light is the light that is scattered by the adjacent tissue volume and received by the light detecting portion of the optical sensor. The term "attenuation" measurement as used herein generally refers to a measure of the attenuation of light due to absorption and scattering by tissue along the optical path of the sensor. The measured attenuation may therefore not be an exact measurement of the actual light absorption by the tissue volume since light reflections and scattering may cause attenuation of the remitted light intensity not attributed to actual light absorption by the tissue.

Alternatively, the emitted intensity $i_{in}$ for each wavelength is measured prior to implantation, e.g., at the time of manufacture, and assumed to be sufficiently stable throughout the usable life of the sensor as to not cause significant measurement error. In this case, a reference photodetector may be eliminated from the light emitting portion of the sensor and thereby reduce overall size and complexity of the sensor. One method for measuring the emitted intensity prior to implantation uses the light detecting portion to measure the remitted light when the sensor is positioned within a calibrated reflective housing. The construction of the emitting portion is designed to minimize or prevent drift in the emitted light intensity over time. Design considerations include minimizing the distance between the tissue and the photonic surfaces of the LEDs (or other light emitting optoelectronic devices included in the emitting portion).

The attenuation for four wavelengths is determined to allow the second derivative with respect to wavelength of the attenuation spectra at the two intermediate wavelengths to be computed. This determination of second derivatives at two intermediate wavelengths allows for computation of a ratio for the two second derivatives as a scaled second derivative. By properly selecting the intermediate wavelengths, a scaled second derivative is an oxygen-dependent and volume-independent ratio and therefore provides a measure of O₂Sat. At block 310, the attenuation measurement for each intermediate wavelength out of the four detected wavelengths is converted to a second derivative (D″), expressed generally as:

$$D''(\lambda_i) = A(\lambda_{i+1}) - 2A(\lambda_i) + A(\lambda_{i-1}) \quad 2$$

wherein $A(\lambda_i)$ is the light attenuation, measured according to Equation 1 above, at the wavelength for which the second derivative is being computed, $A(\lambda_{i+1})$ is the attenuation at the next higher wavelength and $A(\lambda_{i-1})$ is the attenuation at the next lower wavelength of the four wavelengths. Equation 2 assumes equal spacings between the four wavelengths. When unequal spacings are used, a different equation for the second derivative with respect to wavelength is required to account for the different wavelength spacings.

The second derivative of a selected intermediate wavelength is scaled by the other computed second derivative at block 312. In one embodiment, the attenuation is measured for wavelengths at 680 nm, 720 nm, 760 nm, and 800 nm. The second derivatives of the attenuation spectra are computed at 720 nm and 760 nm and the second derivative at 720 nm is scaled by the second derivative at 760 nm. The scaled second derivative (SD") of the 720 nm attenuation can be expressed as $$SD''=D''(720)/D''(760) \quad (3)$$

This SD"(720) is dependent on tissue oxygen saturation and independent of the total hemoglobin and optical path length. The reduced dependence on total hemoglobin and optical path length is expected to reduce the effects of motion artifact on the oxygen measurement.

Once the scaled second derivative is obtained, the stored calibration data is used at block 314 to derive the absolute $O_2$Sat. The second derivative for attenuation at 720 nm wavelength (as well as 760 nm) is dependent on oxygen saturation and total hemoglobin. Thus, at block 316, HbT may be determined knowing the D"(720), or D"(760), with respect to wavelength, the derived absolute $O_2$Sat, and the stored calibration data.

Tissue oxygenation, as defined herein, is a function of both tissue $O_2$Sat and HbT. Depending on the particular tissue oxygenation monitoring application, the derived $O_2$Sat and HbT may each be used separately in a monitoring algorithm or combined to determine a tissue oxygenation index used to monitor a patient's status and/or detect a physiological condition. At block 322, a tissue oxygenation index may be computed as a function of $O_2$Sat and HbT. For example, a tissue oxygenation index may be a weighted combination of the $O_2$Sat and HbT measurements. In one embodiment, a tissue oxygenation index is computed as:

$$TOI=0.8\ O_2\ Sat+0.2\ HbT \quad (4)$$

It is recognized that other weighting factors may be used and the selected weighting factors may even be tailored to an individual patient and a particular monitoring/detection algorithm.

Thus, a tissue oxygenation index computed using absolute measurements of $O_2$Sat and HbT can be available on a continuous or periodic basis in an ambulatory patient. The TOI and/or the individual calibrated values of $O_2$ Sat and HbT may be used for tracking a patient's baseline oxygenation, changes in patient status and in detecting hemodynamically unstable arrhythmias.

The absolute values of $O_2$ Sat, HbT and the TOI computed using the calibrated absolute values of $O_2$ Sat and HbT are computed and stored by the ICD. Additionally, differences between each of these oxygenation measures and a baseline or other earlier corresponding measure may be computed and stored as calibrated trended variables. As such, in addition to storing the absolute values, trended values of each of the oxygenation measurements may be stored as changes in the absolute values over time, referred to as $dO_2$ Sat, dHbT or dTOI, which each represent the difference between a current measurement and a previous measurement of the same calibrated measurement.

Alternatively or additionally, non-calibrated values and trends of the oxygenation measurements may be determined and stored. Since sensor calibration can be time consuming and adds to computational burden for computing a calibrated measurement, it may be desirable to compute non-calibrated values and trends of oxygenation measurements without conversion of those measurements to an absolute value. For example, a scaled second derivative of a properly selected wavelength, SD"(λ), is a volume-independent measure of $O_2$Sat and may be computed as an index of $O_2$Sat without conversion to a calibrated measurement. Likewise, D"(λ), which is volume and oxygen dependent, can provide an index of HbT without conversion to a calibrated measurement. Each of these uncalibrated oxygenation measurements may be used individually as baseline indices of tissue oxygenation or combined in a computation of a TOI, such as a weighted linear combination of the uncalibrated measurements similar to Equation (4) above.

The uncalibrated measurements of SD"(λ), D"(λ), and a TOI computed using SD"(λ) and D"(λ) may be determined and stored at device implant for use as baseline measurements and measured during patient monitoring for monitoring patient status and for use in detecting hemodynamically unstable arrhythmias and controlling device therapies. Trends in each of the uncalibrated measurements over time, referred to as dSD"(λ), dD"(λ), and dTOI, may also be determined and stored as the difference between a current uncalibrated measurement and a previous corresponding measurement. In summary, various algorithms for monitoring a patient's tissue oxygenation status, detecting hemodynamically stable and unstable arrhythmias and controlling arrhythmia therapy may utilize calibrated measurements ($O_2$ Sat and HbT), trends in the calibrated measurements ($dO_2$Sat and dHbt), uncalibrated measurements (SD"(λ) and D"(λ)), and/or trends in the uncalibrated measurements (dSD"(λ) and dD"(λ)).

The oxygen saturation measurement derived from a scaled second derivative is a volume-independent measurement and is therefore expected to have reduced susceptibility to motion artifact, which could alter the optical pathway and thus alter the measurement volume. However, some embodiments may utilize the measured total hemoglobin volume fraction, which is dependent on the measurement volume, to filter or blank tissue oxygenation monitoring during periods in which HbT is out of a normal range, which may be due to motion or activity of the patient.

Accordingly, in one embodiment, the measured HbT is compared to an acceptable range, e.g. between approximately 1% and approximately 25%, at block 318. If HbT is out of the acceptable range, tissue motion may be causing erroneous HbT measurements. At block 320, the tissue oxygenation measurement is blanked or otherwise deemed invalid based on the out-of-range HbT measurement. For example, patient activity may result in oscillatory movements that produce a signal that is intermittently in and out of the acceptable range. Intervals in which the HbT measurement is out-of-range may be blanked for determining a tissue oxygenation index. During intervals in which the HbT measurement is in range, the tissue oxygenation index is computed at block 322. When HbT is out of range, the absolute tissue oxygen saturation measurement may also be ignored or still be determined and stored.

Figure 6:
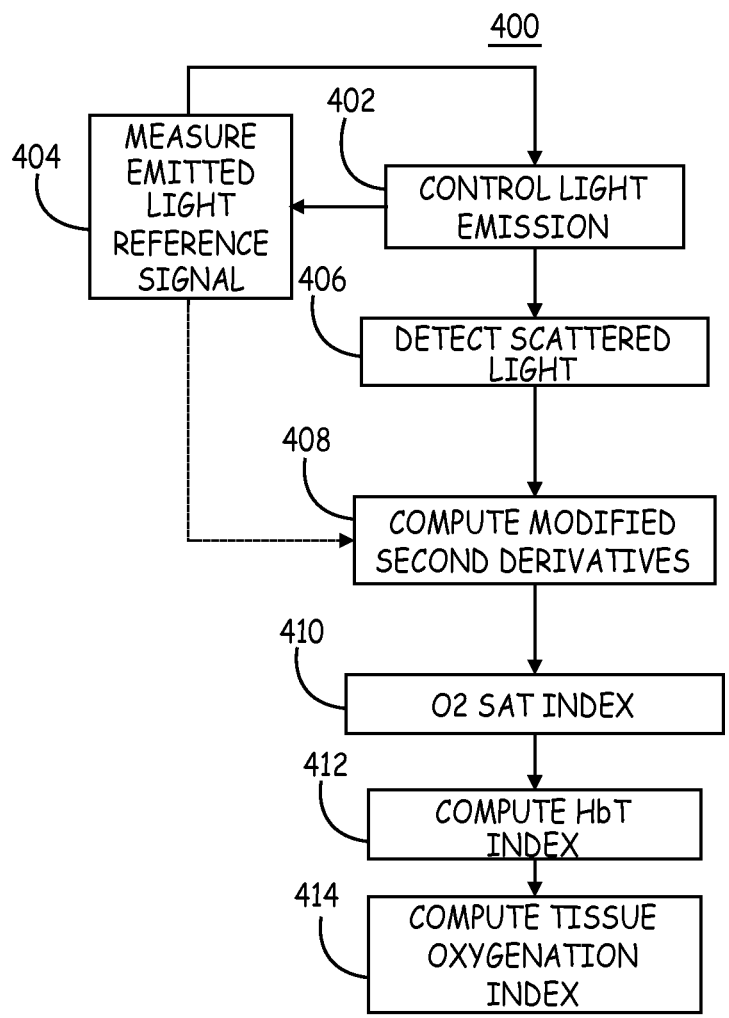
FIG. 6 is a flow chart of an alternative method for using an optical sensor capable of measuring absolute tissue oxygen saturation for monitoring tissue oxygenation.

FIG. 6 is a flow chart of an alternative method 400 for using an optical sensor capable of measuring absolute tissue oxygen saturation for monitoring tissue oxygenation. At block 402, control signals are applied to drive circuitry to control the emission of light from the light emitting portion of the optical sensor.

In one embodiment, a reference photodetector is included in the light emitting portion to provide a reference signal measuring the emitted light. The intensity of the emitted light may be controlled using a reference feedback signal as indicated by block 404. In other methods, a reference photodetector is used to measure the emitted light intensity for computing the attenuation of each wavelength using Equation 1 above. In method 400, the emitted light intensity is measured using the reference photodetector for controlling light emission such that the emitted intensity ($i_{in}$) at each of the wavelengths used for attenuation measurements is maintained within a specified range.

An emitted light reference signal measured at block 404 using the reference photodetector output signal is provided as feedback to the control module controlling light emission at block 402. Drive signals applied to the light emitting portion may be adjusted in response to the emitted light reference signal to maintain the emitted light intensity within a target range for each wavelength selected for attenuation measurements.

When the emitted light is controlled to be maintained within a specified range, the emitted light intensity ($i_{in}$) in the attenuation Equation (1) above becomes a constant. Manipulation of the second derivative Equation (2) above results in a modified second derivative equation:

$$D''(\lambda_i)_{modified} = -\log(i_{out})_{\lambda,i+1} + 2\log(i_{out})_{\lambda,i} - \log(i_{out})_{\lambda,i-1} \quad (5)$$

which may be rewritten as:

$$D''(\lambda_i)_{modified} = C_i + \log\{(_{out})_{\lambda,i2}/((i_{out})_{\lambda,i+1})(i_{out})_{\lambda,i-1})\} \quad (6)$$

The term $C_i$ for a given wavelength $\lambda_i$ becomes a calibration constant. Thus, a modified scaled second derivative may be computed using only the detecting portion output signal and the calibration constants $C_i$ determined for each of the measured wavelengths. In the case where there is no reference measurement for emitted light intensities at each wavelength, but the drive signal to the light sources is controllable, the constants Ci are predetermined functions of the drive signal. Note that the above Equation 6 is written for equal wavelength spacing and will include more terms for non-equal wavelength spacing.

The scattered light is detected by the optical sensor at block 406 and used to compute the modified second derivatives at block 408 at two (or more) intermediate wavelengths. The modified second derivatives need only be computed for two intermediate wavelengths being used to compute $O_2$Sat and HbT.

A simplified scaled second derivative may be used as an estimate of tissue oxygen saturation in which the $C_i$ constants are ignored in the above equations. A simplified scaled second derivative may take the form of:

$$SD'' = \frac{-\log(i_{out})_{\lambda,i+1} + 2\log(i_{out})_{\lambda,i} - \log(i_{out})_{\lambda,i-1}}{-\log(i_{out})_{\lambda,i+2} + 2\log(i_{out})_{\lambda,i+1} - \log(i_{out})_{\lambda,i}} \quad (7)$$

This simplified scaled second derivative may be useful for measuring an uncalibrated, index of $O_2$Sat at block 410. A corresponding uncalibrated index of HbT may be computed at block 412 using the simplified second derivative computed using Equation 6. The $O_2$Sat and HbT indices may be used individually or combined in a TOI computed as a function of both at block 414.

In addition or alternatively to using the emitted light reference signal as feedback to control light emission, the emitted light reference signal may be used by the monitoring module to adjust the computed modified second derivatives at block 408. Shifts in the intensity of the emitted light may be accounted for by introducing a correction term in the equation used to compute the modified second derivative. Accordingly, an adjusted modified second derivative for a selected intermediate wavelength used to compute absolute oxygen saturation might be computed using:

$$D''(\lambda_i)_{modified} = C_i - \log(i_{out} + CT)_{\lambda,i+1} + 2\log(i_{out} + CT)_{\lambda,i} - \log(i_{out} CT)_{\lambda,i-1} \quad (8)$$

wherein CT is a correction term determined for each wavelength using the emitted light reference signal and is used to adjust the remitted light intensities $i_{out}$ for each wavelength. The CT may be a positive or negative value.

In the methods described herein for monitoring patient status, sensor status, detecting hemodynamically unstable arrhythmias and controlling device therapies, the modified second derivative computations may be substituted for second derivative computations used in deriving volume-independent indices of $O_2$Sat and indices of HbT.

Figure 7:
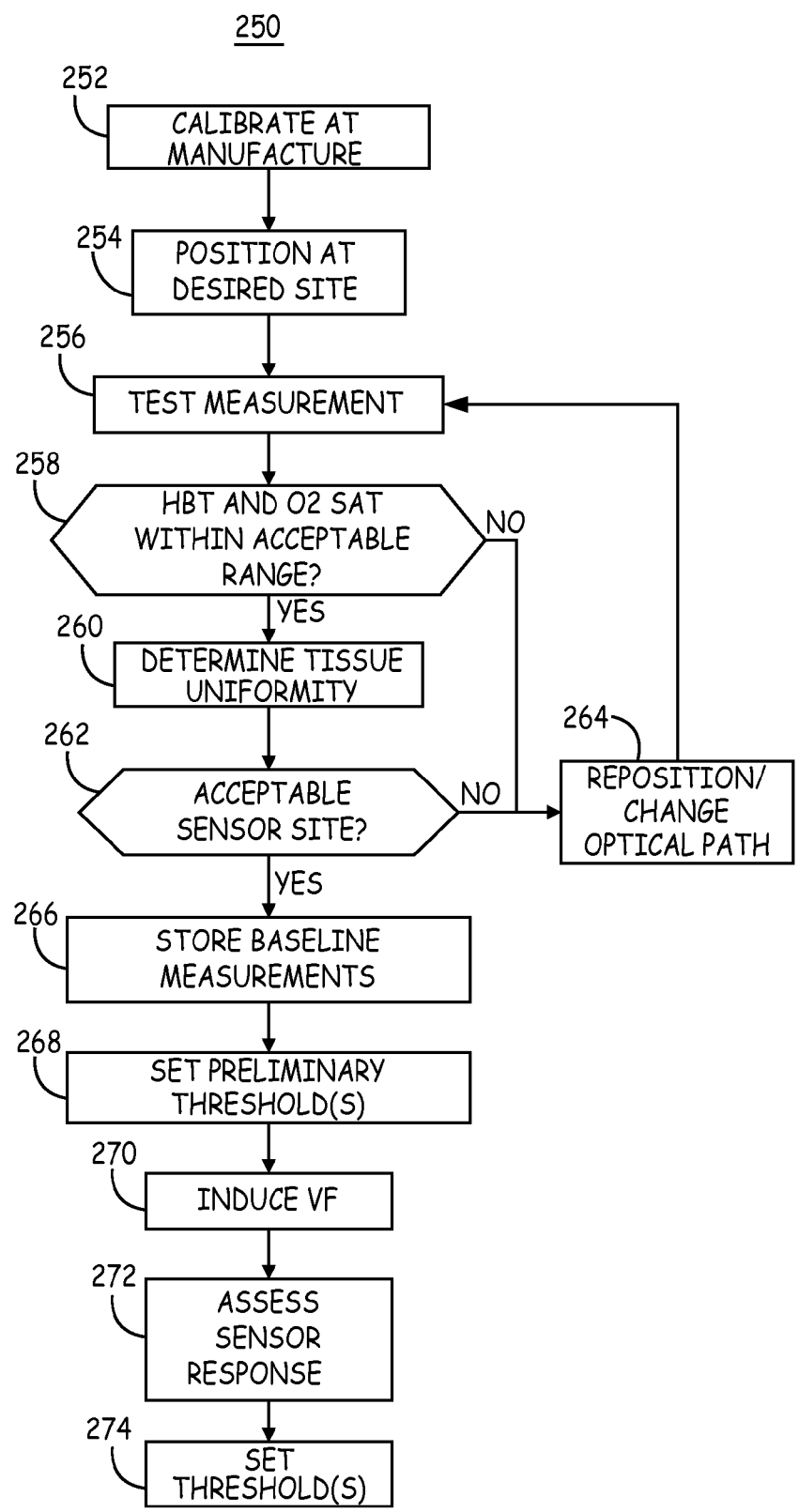
FIG. 7 is a flow chart of a method for using an optical sensor incorporated in an ICD system.

FIG. 7 is a flow chart of a method 250 for using an optical sensor incorporated in an ICD system. At block 252 of method 250, the optical sensor is calibrated using control samples, for example in an in vitro blood circuit, having known oxygen saturation and total hemoglobin concentration. The calibration method may be used to generate a look-up table. A look-up table of values relating measurements computed from the photodetector output signal and the known $O_2$Sat and HbT may be stored in the device memory. The look-up table can then be used to derive absolute $O_2$Sat and Hbt values from an optical sensor measurement as will be further described below.

Alternatively, calibration methods may include curve-fitting methods to solve for coefficients defining best-fit curves to the calibration data. In one embodiment, the absolute tissue oxygen saturation is defined by:

$$O_2\text{sat} = Ae^{B(SD''(\lambda_i))} + C \quad (9)$$

wherein SD" is a scaled second derivative of the attenuation spectra at a selected intermediate wavelength ($\lambda_i$) emitted and detected by the optical sensor. As described above, a scaled second derivative of the attenuation spectra at a selected wavelength is determined by the monitoring module using the photodetector signal. The scaled second derivative is the ratio of the second derivative with respect to wavelength of the attenuation spectra at a selected wavelength $\lambda_i$ to the second derivative of the attenuation spectra at another selected wavelength used for scaling. By properly selecting the wavelength $\lambda$ and the other wavelength used for scaling, the scaled second derivative is an oxygen-dependent and volume-independent ratio. The coefficients A, B and C are determined through best-fit analysis of measurements of the scaled second derivative for calibration samples having known oxygen saturation.

The total tissue hemoglobin volume fraction can be defined by the equation:

$$\text{HbT} = [M(100 - O_2\text{Sat})^N + L] * [(D''(A)_{\lambda,i}/d\lambda)/SF] \quad (10)$$

wherein M, N, and L are coefficients determined during calibration and $D''(A)_{\lambda,i}/d\lambda$ is the second derivative of the attenuation spectra with respect to wavelength at the selected intermediate wavelength $\lambda_i$. The second derivative of the attenuation spectra with respect to wavelength at a given wavelength is also referred to generally herein as $D''(\lambda)$. $D''(\lambda)$ is measured for samples containing known total hemoglobin volume fraction and known oxygen saturation. The calibration coefficients M, N and L may then be computed for a best-fit of the measured second derivative values and known $O_2$ Sat and HbT. Alternatively, the measured second derivative values and known $O_2$Sat and HbT may be used to generate a look-up table for converting the measured second derivative values to HbT.

SF is a spacing factor which may be used to adjust for an emitting-to-detecting portion spacing that may be different during measurements than that used during calibration. Since the HbT measurement is dependent on both $O_2$Sat and the measurement volume, and measurement volume is dependent on the optical pathway defined at least in part by the spacing between the emitting and detecting portions, the HbT measurement needs to be corrected for changes in emitting-to-detecting portion spacing. For example, the sensor may be calibrated using a nominal emitting-to-detecting portion spacing, however when multiple emitting and/or detecting portions are selectable in a sensor or combination of sensors, the spacing may be different during monitoring than that used during calibration. As such, a spacing factor corresponding to selectable emitting and detecting portions may be stored and used to correct the HbT measurement when a different spacing is used during monitoring than during calibration.

At block 254, the sensor is positioned at a desired implant site (or external site in the case of an external device to be worn by the patient). A test measurement is performed at block 256. The absolute $O_2$Sat and HbT are determined from the sensor output signal using the stored calibration data. The measured values are compared to an acceptable measurement range at block 258. This comparison may be performed manually or automatically using a programmed range stored in the medical device memory. An acceptable measurement range generally corresponds to an expected physiological range for $O_2$Sat and HbT. For example, an acceptable range for tissue $O_2$Sat might be defined to be between approximately 80% and 90%, but may be determined clinically. An acceptable range for HbT might be defined to be between approximately 1% and 25%. These ranges may vary depending on the type of tissue adjacent to the sensor, the heterogeneity of the tissue, the oxygenation state of the patient and other factors. The acceptable measurement range may be defined nominally or tailored to a given patient.

If the tissue oxygen saturation exceeds a predefined expected range, for example greater than approximately 90%, the sensor may be in a position that results in arterial blood strongly contributing to the tissue oxygen saturation measurement. If the monitoring application is concerned with measuring tissue oxygenation, e.g. in skeletal muscle, rather than arterial oxygen saturation, the sensor may be repositioned at block 264.

Likewise, if the oxygen saturation is too low, for example less than approximately 80%, the sensor may be in a position that results in venous blood strongly contributing to the oxygen saturation measurement. If the absolute oxygen saturation falls below an expected physiological range for the particular sensing application, the sensor may be repositioned at block 264.

If the total hemoglobin is less than a predetermined range, for example less than approximately 1%, the sensor may be improperly positioned against the tissue (poor tissue contact) or in a position over a non-tissue medium or low or non-perfused tissue. For example, if the sensor is positioned over fat, scar tissue, clear body fluids, or other implanted medical device components, the total tissue hemoglobin concentration may be below a normal physiological range for perfused tissue. A total tissue hemoglobin of greater than an acceptable physiological range, for example greater than approximately 25%, may indicate blood pooling in the measurement volume beneath the sensor or other sensor measurement error. If the HbT test measurement is outside a predefined acceptable range, the sensor may be repositioned at block 264. Instead of repositioning the sensor at block 264, a selected optical path may be changed when multiple light emitting and detecting pairs are available to select from for monitoring tissue oxygenation.

Once the $O_2$Sat and HbT measurements are confirmed to be in an acceptable physiological range for the tissue being monitored, at block 258, a tissue uniformity index may be determined at block 260. A tissue uniformity index is determined by utilizing at least two different emitting-to-detecting portion spacings. Accordingly at least two different combinations of light sources and light detectors at two different spacings must be available, on the same or different optical sensors, positioned adjacent a target tissue volume.

When at least two different spacings are available, the absolute tissue oxygen saturation is measured using the two different spacings and compared. A tissue uniformity index may be computed based on the difference between two or more measurements performed using different emitting-to-detecting portion spacing. Each measurement would each involve different measurement volumes defined by different measurement pathways extending through the tissue. For example, a relatively greater emitting-to-detecting portion spacing would result in greater depth of the measurement pathway and measurement volume.

If the difference between two measurements is small, the tissue is relatively homogeneous and uniform through the depth of the larger measurement volume. If the difference between two measurements is large, the tissue is more heterogeneous or non-uniform in oxygenation. A threshold for detecting uniform, homogenous versus non-uniform, heterogeneous tissue volumes may be selected according to a particular application. Detection of heterogeneous tissue may warrant repositioning of the sensor. A tissue uniformity index may indicate the most appropriate emitter-to-detector spacing for measuring within a desired tissue volume and therefore guide selection of light sources and light detectors when multiple combinations are available.

In summary, the initial $O_2$Sat, HbT, and tissue uniformity measurements can be used individually or in combination to decide if the sensor position is acceptable at block 262. If not the sensor may be repositioned at block 264. Instead of repositioning the sensor when unacceptable tissue uniformity or HbT or $O_2$Sat measurements are obtained, a different optical path may be selected at block 264 by selecting a different combination of light source(s) and light detector when available. For example, multiple light sources and light detectors may be available in one or more sensors to allow selection of different optical paths.

If the sensor position is acceptable, the sensor is fixed at the desired site, and baseline $O_2$Sat and HbT measurements may be acquired and stored at block 266 according to the needs of the particular sensing application. Baseline measurements may be acquired for comparison to future measurements, for use in learning algorithms performed during clinical interventions or during spontaneously occurring arrhythmias for use in setting thresholds for detecting arrhythmias and discriminating hemodynamically stable and unstable forms of arrhythmias, or for initiating continuous monitoring of the tissue $O_2$Sat and HbT, i.e. tissue oxygenation, for monitoring patient status.

At block 268 preliminary detection thresholds are set for discriminating hemodynamically stable arrhythmias from hemodynamically unstable arrhythmias. A detection threshold may be set based on a percentage change or other defined interval from the baseline measurements.

When HbT and/or $O_2$Sat measurements are out of an acceptable range and a different emitting-to-detecting portion spacing is not available or respositioning at block 264 is not possible, or otherwise not performed, baseline measurements may still be stored at block 266 and used for setting patient-specific thresholds at block 268. Patient-specific thresholds of HbT and $O_2$Sat, or a tissue oxygenation index computed from the HbT and $O_2$Sat measurements, may be defined and stored for use in detecting and discriminating arrhythmias.

For example, if the $O_2$ Sat measurement is low, e.g. <80%, the sensor may be located near a vein and the contribution of the venous blood in the optical path may be causing the lower measurement. In this case, a change in $O_2$Sat and HbT during a hemodynamically unstable arrhythmia may be reduced compared to a measurement that is obtained over a capillary bed. Likewise if a high arterial blood contribution is present in the measurement due to the sensor being located over an artery, the baseline $O_2$Sat will be higher than when positioned over a capillary bed. A change in $O_2$Sat during a hemodynamically unstable arrhythmia may again be lower than when the sensor is over a capillary bed. As such, thresholds relating to $O_2$Sat and HbT and thresholds relating to changes in $O_2$Sat and HbT that are used for detecting hemodynamically unstable arrhythmias may be adjusted according to baseline measurements. For example, a threshold change in $O_2$Sat for detecting ventricular fibrillation may be lowered when the initial baseline $O_2$Sat measurement is lower (higher venous contribution) or higher (higher arterial contribution) than an expected baseline measurement (or acceptable measurement range) corresponding to positioning over a capillary bed.

After setting preliminary thresholds at block 268, arrhythmia induction is performed at block 270. Current clinical practice includes inducing a ventricular fibrillation (VF) episode during an ICD implantation procedure to verify an acceptable defibrillation shock threshold. After inducing VF, the optical sensor response is assessed at block 272. For example measurements obtained continuously or a predefined time points at baseline, episode onset, and during the episode may be compared to assess the change in $O_2$Sat, HbT, and/or a tissue oxygenation index computed from the measured $O_2$Sat and HbT. Changes in the oxygenation measurements and comparisons of the measurements to the preliminary thresholds set at block 268 can be used to determine if an appropriate detection of a hemodynamically unstable arrhythmia is made during the induced VF.

Adjustment of the preliminary threshold(s) may be made based on the sensor response. Adjustments may be made manually or automatically by the device. If an appropriate detection is made, the preliminary thresholds are accepted and set as the detection thresholds at block 274. If not, the thresholds are adjusted appropriately based on the oxygenation measurements during the induced VF episode. If an appropriate detection is made, but a large difference exists between the threshold(s) and the oxygenation measurements, the threshold may be adjusted to provide greater specificity to VF detection.

Figure 8:
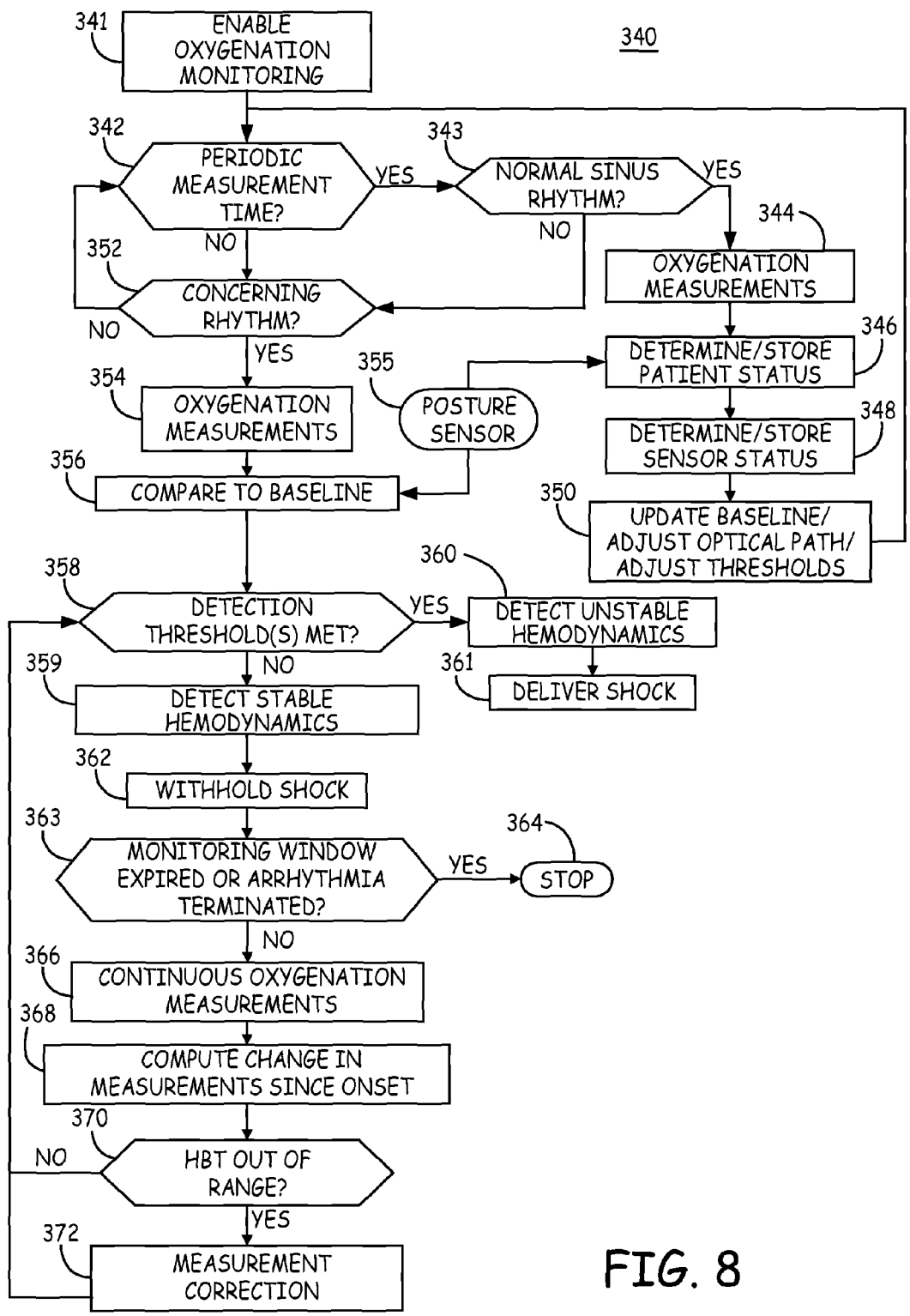
FIG. 8 is a flow chart of a method for monitoring patient status and controlling arrhythmia therapy delivery.

FIG. 8 is a flow chart of a method 340 for monitoring patient status and controlling arrhythmia therapy delivery. At block 341, oxygenation monitoring is enabled. Oxygenation monitoring may be enabled at the time of device implantation based on acceptable sensor positioning, baseline measurements, and sensor response to an induced arrhythmia episode.

Tissue oxygenation measurements may be performed on a periodic basis for assessing patient status, sensor function, and resetting baseline measurements or adjusting detection thresholds. Additionally, tissue oxygenation measurements are performed on a triggered basis upon detecting a concerning arrhythmia episode. At block 342, the device determines if it is time to perform periodic measurements, e.g. based on expiration of a periodic timer. Periodic measurements may be obtained at any desired time interval, for example hourly, daily or weekly. Periodic time measurements may be adjusted automatically or manually if measurements are desired on a more or less frequent basis. For example, if a change greater than a predetermined percentage or predefined range is detected since a previous measurement, the frequency of periodic measurements may be increased to allow closer monitoring of patient status.

If it is time for performing periodic measurements, the ICD confirms the patient is in normal sinus rhythm at block 343. Normal sinus rhythm can be verified based on regular EGM event intervals (P-P intervals and/or R-R intervals) occurring at a rate less than a tachycardia detection rate. If normal sinus rhythm is not verified at block 343, method 340 advances to block 352 to determine if the rhythm is a concerning rhythm that requires tissue oxygenation monitoring. If normal sinus rhythm is present, the oxygenation measurements are performed at block 344. Performing tissue oxygenation measurements involves computing the uncalibrated $SD''(\lambda)$ and $D''(\lambda)$ values. These values may be stored as indices of $O_2$Sat and HbT or converted to calibrated absolute $O_2$Sat and HbT measurements using stored calibration data when available. A TOI may then be computed using the uncalibrated $SD''(\lambda)$ and $D''(\lambda)$ values and/or the calibrated $O_2$Sat and HbT.

At block 346, the measurements are stored and may be used to determine a patient status. For example, a patient tissue oxygenation status may be indicated as hypoxic or normal based on the oxygenation measurements. A hypoxic status may warrant more frequent patient monitoring or generating a warning provided to the patient or to a clinician.

A patient posture signal may be provided as input when determining patient status as indicated by block 355. For example, in one embodiment, an accelerometer is used for detecting a patient position (or optical sensor position). The patient position is used to store different tissue oxygenation measurements according to patient position and for determining different baseline tissue oxygenation measurements according to patient position. Detection of a patient status may take into account both the patient (or sensor) position and the oxygenation measurement.

At block 348, the oxygenation measurements may be used to determine and store a status of the optical sensor. If either of the $O_2$Sat or HbT measurements (or $SD''(\lambda)$ and $D''(\lambda)$) are out of the acceptable measurement range, the sensor status may be indicated as unreliable. Tissue oxygenation measurements may be temporarily or permanently disabled based on out of range measurements.

The oxygenation measurements performed at block 344 and determination of sensor status at block 348 may be analogous to the measurements and comparisons performed at the time of device implant (with the exception of an induced arrhythmia) as discussed in conjunction with FIG. 7. In other words, comparisons to acceptable measurement ranges and a measured tissue uniformity index may be used to select a new combination of light source(s) and light detectors (when available) to change the optical path of the sensor, update stored baseline measurements, and/or adjust the detection thresholds applied to the oxygenation measurements as indicated at block 350.

When a concerning arrhythmia is detected at block 352, oxygenation measurements are performed at block 354 and stored as arrhythmia episode "onset" measurements. An arrhythmia may be initially detected based on EGM sensing. Arrhythmia detection methods may include EGM event interval and/or EGM morphology analysis. Tissue oxygenation monitoring may be initiated at block 354 in response to any arrhythmia detection or in response to certain types of arrhythmia detection defined as "concerning" arrhythmias.

In one embodiment, a "concerning" arrhythmia is an EGM-based arrhythmia detection associated with a fast ventricular rate falling in a fast ventricular tachycardia (VT) or a VF detection rate zone. A "concerning" arrhythmia may also be defined to include an arrhythmia that cannot be discriminated between an atrial arrhythmia (supraventricular arrhythmia) and ventricular arrhythmia, e.g. due to approximately equal atrial and ventricular rates with 1:1 correspondence between atrial and ventricular events. Such arrhythmias may originate in the atria in which case a ventricular shock therapy is not needed. In other embodiments, a "concerning" arrhythmia may be any arrhythmia exceeding a predetermined rate, in particular any arrhythmia detected in response to a fast ventricular rate which may be a hemodynamically unstable, potentially lethal arrhythmia.

In some cases, oversensing of the EGM/ECG signal (e.g. T-wave sensing) or other lead related issues (e.g. internal short) may cause erroneous sensing and detection of an arrhythmia. Tissue oxygenation monitoring can be used to confirm hemodynamic stability when arrhythmia detection criteria are met due to erroneous sensing and thereby reduce the occurrence of unnecessary shocks.

Oxygenation measurements are used to determine if the concerning arrhythmia is hemodynamically unstable. If the patient is experiencing a hemodynamically unstable ventricular arrhythmia, a shock therapy may be delivered according to a programmed schedule (or immediately) to restore stable hemodynamic function as quickly as possible. When a fast ventricular arrhythmia is detected but the patient remains hemodynamically stable, a shock therapy may be delayed or withheld to allow spontaneous termination of hemodynamically stable arrhythmia, additional arrhythmia discrimination algorithms and/or less aggressive arrhythmia therapies, such as anti-tachycardia pacing therapies to be delivered in an attempt to avoid delivery of a shock.

At block 354, $O_2$Sat and HbT are measured. Alternatively, during an arrhythmia episode, the uncalibrated measurements may be computed without conversion to absolute, calibrated values. During an arrhythmia episode, the use of the uncalibrated values ($SD''(\lambda)$ and $D''(\lambda)$) may save processing time allowing a trend in tissue oxygenation measurements that indicates poor oxygenation (and hemodynamic compromise) to be detected more quickly.

If the oxygenation measurements are still within the predetermined acceptable measurement range, indicating proper sensor operation, the measurements are compared to baseline oxygenation measurements in conjunction with the stored detection thresholds.

Stored detection thresholds applied to tissue oxygenation measurements at block 358 are defined for detecting the hemodynamic status of the patient. The stored thresholds correspond to discriminating between acceptable tissue oxygenation and low tissue oxygenation that may lead to tissue hypoxia or anoxia. As such, tissue oxygenation measurements are used in method 340 to determine the hemodynamic status of an arrhythmia already detected using EGM/ECG signals, alone or in combination with other sensor signals. Tissue oxygenation measurements are not used as a primary signal for arrhythmia detection. It is contemplated, however, that in other embodiments, the tissue oxygenation measurements may be combined with the EGM/ECG signals and/or other sensor signals to make the initial arrhythmia detection in a multi-parameter arrhythmia detection analysis.

If the onset oxygenation measurements represent a large change from baseline, the patient may already be in a state of hemodynamic compromise. For example the patient may be experiencing a slow onset arrhythmia in which hemodynamic collapse has already begun or occurred. The concerning arrhythmia is detected as hemodynamically unstable at block 360. A shock therapy may be delivered immediately at block 361 (or according to a programmed schedule).

A detection threshold applied to onset oxygenation measurements may be defined separately from detection thresholds used later in the episode. For example a relatively large change in tissue oxygenation measurements, such as an approximately 50% drop in TOI, may be required to immediately deliver a shock in response to onset tissue oxygenation measurements.

If the detection threshold criteria defined for the onset oxygenation measurements are not met at block 358, an default stable hemodynamic status is detected at block 359 (since it may be too early after arrhythmia detection to ascertain the hemodynamic stability of the arrhythmia) and shock therapy is not yet warranted or accelerated as indicated at block 362.

The oxygenation measurements are continuously updated and monitored at block 366 as long as a measurement time window has not expired or the arrhythmia has not terminated, e.g., based on EGM signal analysis, as determined at block 363. A measurement window set in response to a concerning arrhythmia may be set to approximately 10 seconds, without limitation. The tissue oxygenation measurements may be updated upon each sample data point or based on an average or median of multiple sample data points.

A difference between an updated oxygenation measurement and the episode onset measurement may then be determined at block 368 as the change in the measurement since the episode onset. The trend(s) are then compared to a detection threshold at block 358. The difference may be a trend in $O_2$Sat ($dO_{2Sat}=O_2$ Sat$_i$ – $O_2$ Sat$_{onset}$), HbT (dHbT=HbT$_i$–Hb-T$_{onset}$) and/or a TOI (dTOI=TOI$_i$–TOI$_{onset}$), computed as a function of both $O_2$ Sat and Hbt. The trend may alternatively be computed for the uncalibrated indices of $O_2$ Sat, HbT and/or a TOI computed therefrom, i.e. $dSD''(\lambda)$ and $dD''(\lambda)$ and/or dTOI wherein the TOI is computed as a function of both $SD''(\lambda)$ and $D''(\lambda)$. A threshold applied to the trends may be defined for each of the oxygenation measurements independently or a single threshold may be defined for the TOI. For example, a detection threshold applied to $dO_2$Sat might be defined as a 5% decrease from the onset O-$_2$Sat. If the onset $O_2$Sat is 85%, 5% of the onset $O_2$Sat is 4.25%. As such, if the $O_2$Sat at onset is 85% and falls to 80% within a 10 second measurement window, the $dO_2$Sat of 5% is greater than the detection threshold of a 4.25% decrease resulting in the $dO_2$Sat detection criteria being met. Other detection thresholds may be similarly applied to the trended HbT and/or TOI measurements.

If the detection threshold(s) defined for the trended measurements computed during the concerning arrhythmia episode are met or exceeded, as determined at block 358, the hemodynamic status is detected as hemodynamically unstable at block 360. A shock therapy may be delivered immediately or as scheduled at block 361. If the tissue oxygenation measurements correspond to adequate or stable tissue oxygenation, the hemodynamic status is detected as stable at block 359. The shock therapy is withheld at block 362.

During baseline comparisons at block 356 and/or application of detection thresholds at block 358, a posture sensor signal may be provided as input as indicated by block 355. The posture sensor signal is provided for selecting the appropriate baseline measurement and/or detection threshold to be applied to the oxygenation measurements based on a currently measured patient posture. For example, if it is determined that the patient is in a horizontal position on his stomach, corresponding changes are made to the baseline measurement applied to account for the sensed postured of the patient. In one embodiment, for example, the applied baseline measurement is reduced by a clinically established amount, such as 5-10 percent.

In some embodiments, detection thresholds may be defined based on a Principal Component Analysis (PCA) of the tissue oxygenation measurements. PCA involves plotting the $O_2$Sat and HbT measurements (or uncalibrated indices thereof) in a two-dimensional space (or an n-dimensional space when additional physiological variables are being used in combination with the oxygenation measurements). A vector identifying a first principal component of variation of the plotted measurements is computed. The first principal component of variation of the measurements may be identified for different types of heart rhythms and used as a template for detecting a given arrhythmia when the first principal component of the variation of the oxygenation measurements approaches a stored first principal component template for the given arrhythmia.

Additionally or alternatively, a vector identifying a first principal component of variation of the plotted measurements during various confounding situations, such as during motion or known patient activities or postures, may be determined for use in artifact removal. In this case, a principal component that is normal (orthogonal) to the first principal component of the plotted measurements in the presence of artifact can be used to remove the effect of the artifact from the measurement variation. Principal component analysis methods generally described in U.S. Pat. Appl. No. 61/144,943 to Deno, et al., incorporated herein by reference in its entirety, may be adapted for use with the tissue oxygenation measurements described herein. For example, an n-dimensional measurement undergoing PCA may include $O_2$Sat and HbT or the uncalibrated values of $SD''(\lambda)$ and $D''(\lambda)$ as two of the n dimensions. Alternatively, a TOI computed using a combination of $O_2$Sat and HbT or $SD''(\lambda)$ and $D''(\lambda)$ may be included as one of the n-dimensions combined with other physiological variables such a measurement obtained from an EGM signal or other hemodynamic measurements.

If a monitoring window expires at block 363, tissue oxygenation monitoring may stop at 364. In some embodiments, a monitoring window may be terminated to prevent prolonged delay of an arrhythmia therapy due to tissue oxygenation monitoring. In other embodiments, a new monitoring window may be started if the arrhythmia is still being detected.

As long as the detection thresholds are not met at block 358 during the monitoring window, the hemodynamic status is determined to be stable at block 359, and a shock therapy is withheld at block 362. At block 370, the HbT measurement may be monitored to detect an out of range measurement. Sample data points corresponding to an out-of-range or questionable value of HbT may be ignored or used to rank the quality of oxygenation measurements in a measurement correction operation at block 372. For example, if a weighted combination of variables is being used to detect hemodynamic stability/instability, less weighting may be applied to HbT (and optionally $O_2$Sat) when HbT measurement(s) are out of an acceptable range. HbT may be ignored or assigned a low weighting based on the range in which the HbT measurement falls. $O_2$Sat may be used alone in determining a tissue oxygenation status. If HbT is significantly out of range for a large number of sample points, detection of a hemodynamically unstable arrhythmia based on oxygenation measurements may be disabled. A predetermined number of minimum sample points falling within an acceptable measurement range during a monitoring window may be required to rely on the oxygenation-based detection algorithm outcome.

Figure 9:
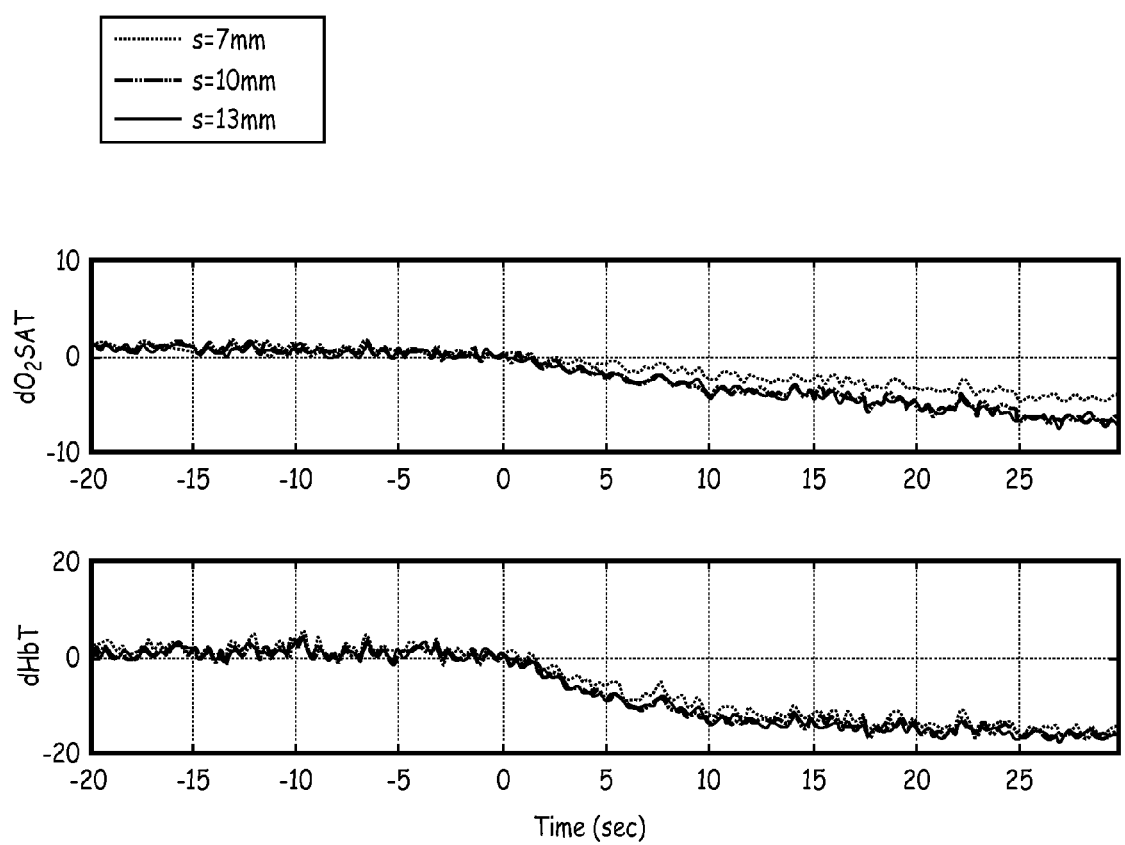
FIG. 9 is a time-based plot of response curves for calibrated trends in $O_2$Sat and HbT during induced ventricular fibrillation in a canine subject.

FIG. 9 is a time-based plot of response curves for calibrated trends in $O_2$Sat and HbT during induced VF in a canine subject. The plotted $dO_2$Sat and dHbT are expressed as percentages of baseline measurements. Attenuation spectra were measured at 680 nm, 720 nm, 760 nm and 800 nm and the $SD''(720)$ nm and $D''(720)$ were used to compute calibrated $O_2$Sat and HbT sample points from which the plotted trends were computed. Three different spacings between the light sources and the light detector were used including 7 mm, 10 mm and 13 mm. The results for the three different spacings are plotted and each show similar trends.

VF induction occurs at time zero. A declining trend in both $O_2$Sat and HbT is observed beginning at the onset of the induced VF. Using appropriate detection thresholds applied to the trended variables, for example in the range of an approximately 2% to an approximately 10% decrease in the trended measurement, hemodynamically unstable arrhythmia can be confirmed within the first 5 to 10 seconds of the onset of VF.

Response curves similar to those shown in FIG. 9 may be acquired and displayed to a clinician during ICD implantation to allow the clinician to select a sensor implant site, select emitting-to-detecting portion spacings when multiple light sources and/or light detectors are available, storing baseline measurements, and setting detection thresholds. Plots similar to those shown in FIG. 9 may also be generated using stored tissue oxygenation data acquired during detected arrhythmia episodes for later review and analysis by a clinician.

Figure 10:
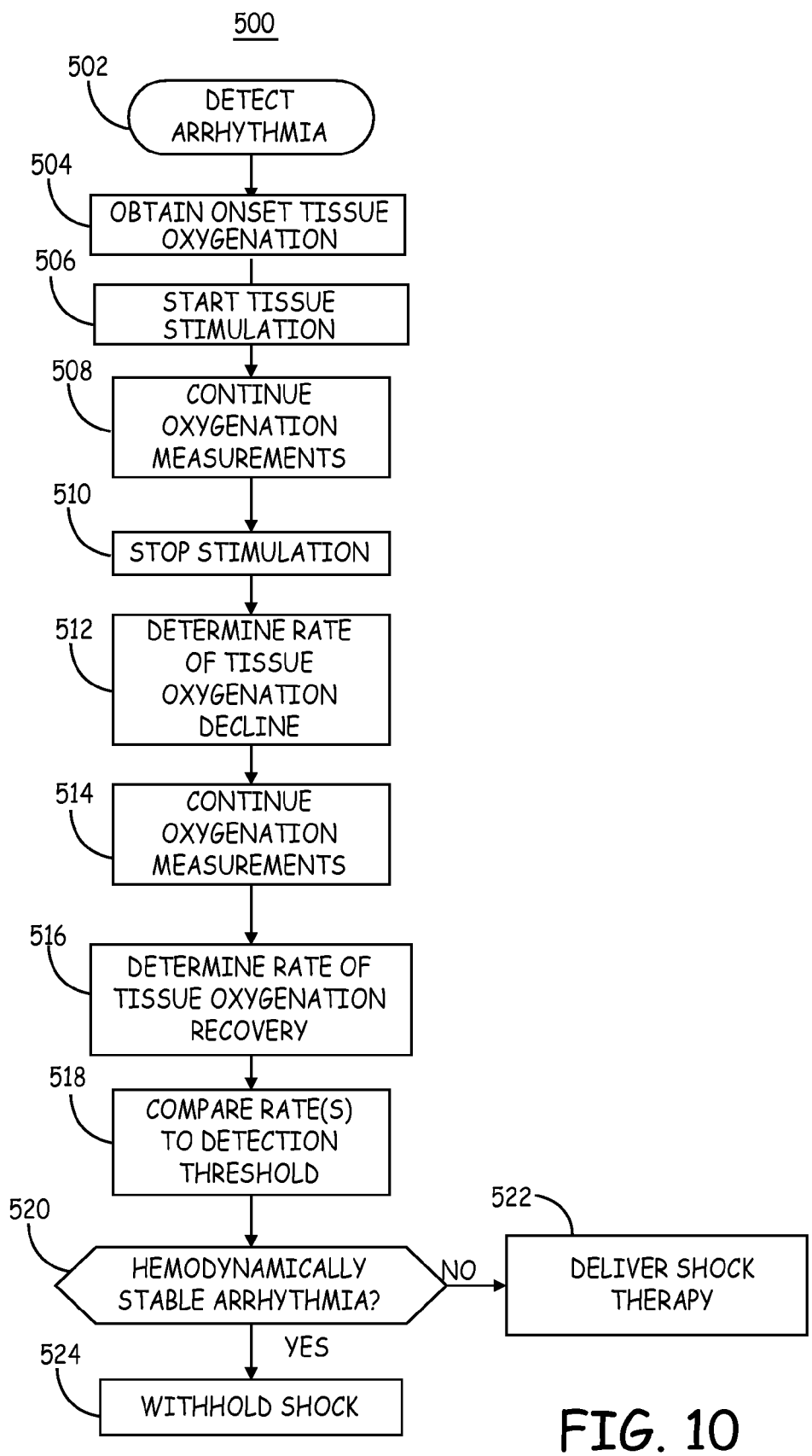
FIG. 10 is a flow chart of an alternative method for controlling arrhythmia therapy using an optical sensor for monitoring tissue oxygenation.

FIG. 10 is a flow chart of an alternative method 500 for controlling arrhythmia therapy using an optical sensor for monitoring tissue oxygenation. In response to detecting an arrhythmia at block 502 using other sensor signals, onset tissue oxygenation measurements are obtained at block 504 as generally described above. At block 506, local electrical stimulation of tissue adjacent to the optical sensor is initiated to increase the metabolic demand (the rate of oxygen consumption by the tissue). Local electrical stimulation of tissue stimulation may be performed using electrodes located along a housing containing the optical sensor or using electrodes located on an electrical lead extending from an optical sensor device or another IMD. Oxygenation measurements may be sampled continuously during the tissue stimulation or obtained at predefined discreet time points or at a single time point during or upon termination of tissue stimulation.

At block 510, tissue stimulation is stopped. Tissue oxygenation measurements are obtained at block 508 for at least one time point subsequent to initiating tissue stimulation to allow a rate of tissue oxygenation decline to be determined at block 512. The rate of tissue oxygenation decline may be determined as $dO_2$Sat, dHbT, dTOI, $dSD''(\lambda)$, $dD''(\lambda)$ or any combination thereof and may be determined as a change relative to the onset measurement.

At block 514, tissue oxygenation measurements may be continued for a predetermined time interval or sampled at one or more discrete time points following termination of tissue stimulation. Tissue oxygenation measurements are obtained for at least one additional time point after stopping tissue stimulation to allow a rate of tissue oxygenation recovery to be determined at block 516. The rate of tissue oxygenation recovery may also be determined as $dO_2$Sat, dHbT, dTOI, $dSD''(\lambda)$, $dD''(\lambda)$ or any combination thereof. The rate of tissue oxygenation recovery may be determined as a change relative to the onset measurement, a minimum tissue oxygenation measurement obtained after initiating tissue stimulation, or the tissue oxygenation measurement obtained upon terminating stimulation.

At block 518, the rate of decline and/or the rate of recovery are compared to previously defined thresholds for detecting a hemodynamically stable arrhythmia. If the rate of decline is less than a detection threshold, and/or the rate of recovery is greater than a detection threshold, the arrhythmia is determined to be hemodynamically stable at block 520 and a shock may be withheld at block 524. If the rate of decline exceeds a detection threshold and/or the rate of recovery is less than a detection threshold, the arrhythmia is determined to be hemodynamically unstable at block 520. The ICD may proceed with delivering a scheduled shock therapy at block 522, either immediately or according to a programmed menu of tiered therapies.

Method 500 is not limited to using tissue oxygenation measurements obtained using an optical sensor capable of measuring light attenuation at four or more wavelengths. In some embodiments, tissue oxygenation measurements obtained in combination with local tissue stimulation as described in conjunction with FIG. 10 may include a non-calibrated index of oxygen saturation determined using a two-wavelength optical sensor, typically emitting and detecting red and infrared light, as generally disclosed in U.S. Patent Application No. 2007/0255148 (Bhunia), hereby incorporated herein by reference in its entirety. In other embodiments, tissue oxygenation measurements obtained in combination with local tissue stimulation may include non-calibrated indices of oxygen saturation and/or blood volume determined using a two-wavelength (typically red and infrared) optical sensor or a three-wavelength (typically red, isosbestic and infrared) optical sensor as generally described in U.S. Patent Publication No. 2008/0208269 (Cinbis, et al), hereby incorporated herein by reference in its entirety. Non-calibrated tissue oxygenation measurements obtained using two- or three-wavelength optical sensors may be substituted for any of the calibrated measurements obtained using four or more wavelength sensors described herein, particularly when a measurement trend is being evaluated over a relatively short period of time, for example, over approximately one minute or less.

Figure 11:
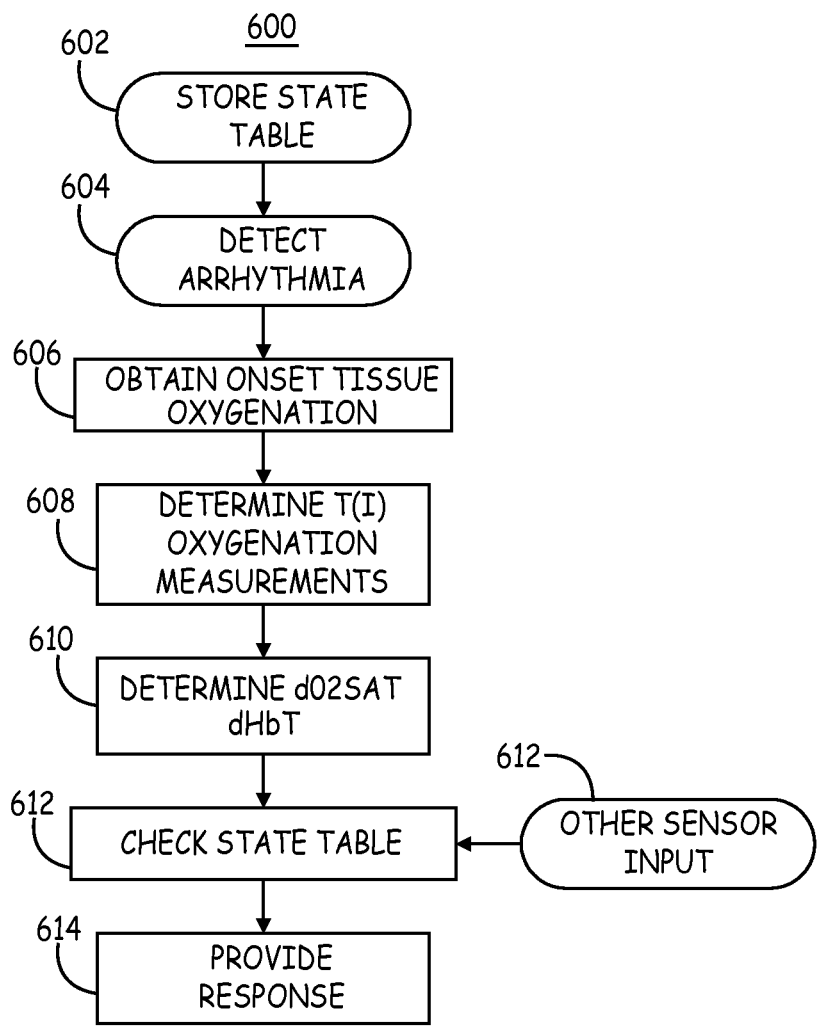
FIG. 11 is a flow chart of a method for detecting a shockable heart rhythm.

FIG. 11 is a flow chart of a method 600 for detecting a shockable heart rhythm. As used herein, a "shockable" heart rhythm is a rhythm that is hemodynamically unstable. A heart rhythm that is hemodynamically stable (even if compromised) maintains tissue oxygenation at or above an acceptable level (which may be below a "normal" tissue oxygenation level). The patient may tolerate a hemodynamically stable rhythm, at least for a period of time, allowing a shock therapy to be withheld or delayed.

Upon onset of an arrhythmia, blood pressure may fall to a reduced but stable level while tissue oxygen saturation in the extremities continues to fall. The stabilized but reduced blood pressure may be the result of peripheral vasoconstriction that occurs in an effort to maintain perfusion and oxygenation of vital organs. The blood pressure is stable but the peripheral body tissue (and eventually vital organs) may become hypoxic.

In other scenarios, blood pressure may fall quickly upon onset of an arrhythmia and then fall at a slower rate. The continued decline in blood pressure is a sign of hemodynamic collapse and will be associated with a continued decline in tissue oxygenation.

Blood pressure will correspond generally to the perfusion of the tissue and thus may be correlated to blood volume or Hbt. Tissue oxygen partial pressure will be correlated to tissue $O_2$Sat. Thus, by monitoring the trends in $O_2$Sat and HbT, as well as their absolute values, reliable discrimination of hemodynamically stable and hemodynamically unstable arrhythmias may be performed.

In method 600, a state table is stored in the memory of an ICD or associated optical sensing device relating state combinations of $O_2$Sat, HbT, $dO_2$Sat and dHbT to a cardiac condition. For example, the absolute values of $O_2$Sat and HbT may classified as high, normal or low according to predefined measurement ranges. The trended measurements, $dO_2$Sat and dHbT, may be classified as increasing, stable or decreasing. For three possible classifications of each of the four variables of $O_2$Sat, HbT, $dO_2$Sat and dHbT, eighty-one possible state combinations exist. Each state combination is then defined to be related to a cardiac status. For example, each state combination may be stored with an associated cardiac status defined as normal, hemodynamically stable but compromised, or hemodynamically unstable. The $O_2$Sat, HbT, $dO_2$Sat and dHbT may be obtained without performing an intervention that alters the tissue metabolic status or with some intervention such as with tissue heating, tissue stimulation, drug delivery or other metabolic or physiologic intervention that alters the state of the tissue or vasculature of the tissue.

An appropriate therapy delivery response for each of the state combinations may also be stored in the state table at block 602. For example, state combinations associated with a normal status may be assigned a withhold therapy response. State combinations associated with a hemodynamically stable but compromised cardiac rhythm status may be associated with one menu of tiered arrhythmia therapies, e.g. excluding a shock delivery, and hemodynamically unstable state combinations may be associated with a more aggressive menu of tiered arrhythmia therapies or immediate shock delivery.

The state table may further include the status or classification of other sensor signals. For example, arrhythmia detection status based on a primary arrhythmia detection sensor signal, such as an EGM or ECG signal, temperature status, activity status, posture status, or any other physiological signal status may be combined in the state table with the tissue oxygenation measurements for determining a cardiac status and associated therapy selection and sequencing. In addition to storing a therapy response, certain state combinations may additionally or alternatively be stored with a device response that includes additional detection, discrimination or diagnostic algorithms to be performed using other sensor signals, different signal processing and analysis methods, and/or include metabolic or physiological perturbation of the tissue, such as tissue stimulation or tissue heating.

At block 604 an arrhythmia may be detected using a primary detection parameter, such as an EGM/ECG signal. At block 606, onset tissue oxygenation measurements are performed, upon detecting an arrhythmia at block 604. Alternatively, tissue oxygenation monitoring as described at blocks 606 through 612 is performed on a continuous basis for use initially detecting a cardiac arrhythmia or an initial cardiac status. A monitoring interval may be defined, which may be approximately 2 seconds, up to approximately 20 seconds or any interval there between, such as approximately 3 seconds, 5 seconds, 10 seconds or 15 seconds. In some applications, even longer monitoring intervals may be applied, e.g., up to approximately one minute. At the beginning of the monitoring interval, the onset oxygenation measurements are acquired at block 606.

At block 608, tissue oxygenation measurements are obtained at one or more time points later than the onset time point and during, or at the end of, the monitoring interval. At least one later measurement for each of O₂Sat and HbT is used to determine dO₂Sat and dHbT, respectively at block 610. At block 612, the absolute O₂Sat and HbT measurements that was obtained at one or more selected time points (onset of a monitoring interval, end of a monitoring interval, or therebetween) are classified according to the possible state table classifications (e.g. high, low, or normal). Likewise the dO₂Sat and dHbT measurements are classified according to the possible state table classifications (e.g. increasing, stable or decreasing). A cardiac rhythm status is determined at block 612 by looking up the status stored with the associated combination of measurement classifications.

As indicated by block 612, other sensor parameter statuses (e.g., temperature, activity, posture, heart rate, etc.) may be provided as input for looking up the cardiac rhythm status in the state table. At block 614, the implantable medical device provides a response based on the identified cardiac rhythm status. As discussed above, the response may include withholding a therapy, selecting a particular menu of tiered therapies, progressing immediately to shock delivery, executing additional detection, discrimination or diagnostic algorithms, or generating a patient/clinician notification.

Thus, a medical device and methods for use have been presented in the foregoing description with reference to specific embodiments. It is appreciated that various modifications to the referenced embodiments may be made without departing from the scope of the disclosure as set forth in the following claims.

The invention claimed is:

1. A method, comprising:
sensing cardiac depolarization signals;
detecting an arrhythmia in response to the depolarization signals;
controlling an optical sensor to emit light in response to the detected arrhythmia;
detecting light scattered by a volume of blood perfused tissue wherein detecting light comprises measuring an optical sensor output signal corresponding to light attenuation of at least four spaced apart light wavelengths;
computing a measure of tissue oxygenation from the optical sensor output signal, wherein computing the measure of tissue oxygenation comprises:
computing a light attenuation for each of the at least four wavelengths;
computing a second derivative of the light attenuation with respect to two different wavelengths;
computing a measure of tissue oxygen saturation independent of total hemoglobin as a ratio of the second derivatives at the two different wavelengths;
computing a measure of total hemoglobin volume fraction using the second derivative of a selected one of the two different wavelengths;
detecting a hemodynamic status of the arrhythmia in response to the measure of tissue oxygenation, wherein the measure of tissue oxygenation is computed responsive to at least one of the measure of tissue oxygen saturation independent of total hemoglobin and the measure of total hemoglobin volume fraction;
computing the measure of tissue oxygenation as a weighted combination of the measure of oxygen saturation and the measure of total hemoglobin volume fraction;
determining if one of the measure of oxygen saturation and the measure of total hemoglobin volume fraction is out of a respective acceptable range; and
adjusting a weighting factor used to compute the weighted combination in response to one of the measures of oxygen saturation and total hemoglobin volume fraction being out of a respective acceptable range.

2. The method of claim 1, wherein detecting a hemodynamic status comprises:
detecting a hemodynamically unstable arrhythmia in response to a decreasing measure of tissue oxygen saturation;
enabling a shock therapy for treating the arrhythmia in response to detecting the hemodynamically unstable arrhythmia; and
withholding delivering of a shock therapy for treating the arrhythmia in response to not detecting the hemodynamic status as being unstable.

3. The method of claim 1, wherein the measure of total hemoglobin volume fraction is computed using the measure of tissue oxygen saturation.

4. The method of claim 1, further comprising:
determining a baseline measurement of tissue oxygenation prior to detecting the arrhythmia;
computing an onset measurement of tissue oxygenation corresponding to a time at which the arrhythmia is detected in response to the depolarization signals;
comparing the baseline measurement and the onset measurement; and
enabling a shock therapy in response to the onset measurement being less than the baseline measurement.

5. The method of claim 1, further comprising:
computing an onset measurement of tissue oxygenation corresponding to a time at which the arrhythmia is detected in response to the depolarization signals;
computing an episode measurement of tissue oxygenation at a time subsequent to arrhythmia detection;
comparing the onset measurement and the episode measurement; and
withholding a shock therapy in response to the comparison.

6. The method of claim 3 further comprising:
defining an acceptable measurement range for the measure of total hemoglobin volume fraction;
comparing the measure of total hemoglobin volume fraction to the acceptable measurement range; and
determining a quality of the measure of total hemoglobin volume fraction in response to the comparing.

7. The method of claim 1, wherein detecting a hemodynamic status comprises:
determining a baseline measurement of tissue oxygenation prior to detecting the arrhythmia;
defining a threshold in response to the baseline measurement; and
comparing the measure of tissue oxygenation to the threshold.

8. The method of claim 3, further comprising computing a tissue oxygenation index as a function of the measure of tissue oxygen saturation and the measure of total hemoglobin volume fraction.

9. The method of claim 1, further comprising:
sensing a signal corresponding to a patient position; and
detecting the hemodynamic status in response to the measure of tissue oxygenation and the signal corresponding to the patient position.

10. The method of claim 1, further comprising:
storing a state table relating the tissue oxygenation measurement to a cardiac status; and
determining an absolute value of the tissue oxygenation measurement and a trended value of the tissue oxygenation measurement, wherein detecting a hemodynamic status comprises determining a cardiac status stored in the state table corresponding to the absolute value and the trended value.

11. An implantable medical device, comprising:
a cardiac electrode for sensing cardiac depolarization signals;
an optical sensor for providing a signal corresponding to light attenuation by a volume of blood perfused tissue;
a control module coupled to the optical sensor controlling the light emitted by the optical sensor;
a monitoring module receiving an optical sensor output signal and measuring light attenuation for at least four spaced-apart light wavelengths; and
a processor coupled to the cardiac electrode and the monitoring module, the processor being configured to:
detect an arrhythmia in response to the depolarization signals,
compute a tissue oxygenation measurement in response to detecting the arrhythmia,
compute an attenuation for each of the at least four wavelengths of detected light,
compute a second derivative of the light attenuation with respect to two different wavelengths,
compute a measure of tissue oxygen saturation independent of total hemoglobin as a ratio of the second derivatives at the two different wavelengths,
compute a measure of total hemoglobin volume fraction using the second derivative of a selected one of the two different wavelengths;
detect a hemodynamic status of the arrhythmia in response to the measure of tissue oxygenation, wherein the measure of tissue oxygenation is computed responsive to at least one of the measure of tissue oxygen saturation independent of total hemoglobin and the measure of total hemoglobin volume fraction;
determine an attenuation for each of the at least four wavelengths at an episode onset time point of the arrhythmia detection;
determine an onset measurement at the episode onset time point based on a weighted combination of the tissue oxygen saturation and the total hemoglobin volume fraction for the time of the arrhythmia detection;
determine if one of the measure of oxygen saturation and the measure of total hemoglobin volume fraction is out of a respective acceptable range; and
adjust a weighting factor used to compute the weighted combination in response to one of the measures of oxygen saturation and total hemoglobin volume fraction being out of a respective acceptable range.

12. The device of claim 11, further comprising a therapy delivery module coupled to the electrode to deliver shock therapy for treating the arrhythmia, wherein the processor is further configured to detect the hemodynamic status as unstable in response to a decreasing measure of tissue oxygenation and to enable the therapy delivery module to deliver the shock therapy in response to detecting the unstable hemodynamic status, and withhold delivery of a shock therapy by the therapy delivery module in response to not detecting the hemodynamic status as unstable.

13. The device of claim 11, wherein the measure of total hemoglobin volume fraction is computed using the measure of tissue oxygen saturation.

14. The device of claim 11, further comprising a therapy delivery module coupled to the electrode for delivering a shock therapy to a patient, wherein the processor is further configured to determine a baseline measurement of tissue oxygenation prior to detecting the arrhythmia, compute an onset measurement of tissue oxygenation corresponding to a time at which the arrhythmia is detected in response to the depolarization signals, compare the baseline measurement and the onset measurement, and enable the therapy delivery module to deliver shock therapy in response to the onset measurement being less than the baseline measurement.

15. The device of claim 11, further comprising a therapy delivery module coupled to the electrode for delivering a shock therapy to a patient, wherein the processor is further configured to determine an onset measurement of tissue oxygenation corresponding to a time at which the arrhythmia is detected in response to the depolarization signals, compute an episode measurement of tissue oxygenation corresponding to a time subsequent to the arrhythmia being detected in response to the depolarization signals, compare the onset measurement and the episode measurement and enable the therapy delivery module to deliver a shock therapy in response to the episode measurement being less than the onset measurement.

16. The device of claim 13, further comprising a memory storing an acceptable measurement range for the measure of total hemoglobin volume fraction, wherein the processor is further configured to compare the measure of total hemoglobin volume fraction to the acceptable measurement range, and determine a quality of the measure of total hemoglobin volume fraction and the measure of tissue oxygen saturation in response to the comparing.

17. The device of claim 11, further comprising a memory for storing a threshold, wherein the processor is further configured to determine a baseline measurement of tissue oxygenation prior to detecting the arrhythmia, compute a threshold in response to the baseline measurement and store the threshold in the memory; and compare the measure of tissue oxygenation to the threshold.

18. The device of claim 13, wherein analyzing the measure of tissue oxygen saturation and the measure of total hemoglobin volume fraction comprises computing a tissue oxygenation index as a function of the measure of tissue oxygen saturation and the measure of total hemoglobin volume fraction.

19. The device of claim 11, further comprising a sensor coupled to the processor to sense a signal corresponding to a patient position, wherein the processor is further configured to detect the hemodynamic status in response to the measure of tissue oxygenation and the signal corresponding to the patient position.

20. The device of claim 11, further comprising a memory storing a state table relating the tissue oxygenation measurement to a cardiac status, wherein the processor is further configured to determine an absolute value of the tissue oxygenation measurement and a trended value of the tissue oxygenation measurement, and detect the hemodynamic status by determining a cardiac status stored in the state table corresponding to the absolute value and the trended value.

21. A non-transitory computer readable medium having computer executable instructions for performing a method comprising:
sensing cardiac depolarization signals;
detecting an arrhythmia in response to the depolarization signals;
controlling an optical sensor to emit light in response to the detected arrhythmia;
detecting light scattered by a volume of blood perfused tissue wherein detecting light comprises measuring an optical sensor output signal corresponding to light attenuation of at least four spaced apart light wavelengths;

computing a measure of tissue oxygenation from the optical sensor output signal, wherein computing the measure of tissue oxygenation comprises:

computing a light attenuation for each of the at least four wavelengths;

computing a second derivative of the light attenuation with respect to two different wavelengths;

computing a measure of tissue oxygen saturation independent of total hemoglobin as a ratio of the second derivatives at the two different wavelengths;

computing a measure of total hemoglobin volume fraction using the second derivative of a selected one of the two different wavelengths; and detecting a hemodynamic status of the arrhythmia in response to the measure of tissue oxygenation, wherein the measure of tissue oxygenation is computed responsive to at least one of the measure of tissue oxygen saturation independent of total hemoglobin and the measure of total hemoglobin volume fraction;

determine an attenuation for each of the at least four wavelengths at an episode onset time point of the arrhythmia detection;

determine an onset measurement at the episode onset time point based on a weighted combination of the tissue oxygen saturation and the total hemoglobin volume fraction for the time of the arrhythmia detection;

determining if one of the measure of oxygen saturation and the measure of total hemoglobin volume fraction is out of a respective acceptable range; and adjusting a weighting factor used to compute the weighted combination in response to one of the measures of oxygen saturation and total hemoglobin volume fraction being out of a respective acceptable range.

22. The method of claim 1, further comprising:
enabling a pulse generator to deliver local stimulation to excitable tissue via electrodes adjacent the optical sensor to increase tissue oxygen consumption when light is being detected by the optical sensor.

23. The method of claim 1, further comprising:
storing a state table relating a plurality of combinations of oxygen saturation independent of total hemoglobin and total hemoglobin volume fraction to a cardiac status; and
determining a cardiac rhythm status from the state table using the measure of oxygen saturation independent of total hemoglobin and the measure of total hemoglobin volume fraction determined in response to detecting the arrhythmia.

24. The method of claim 23, further comprising:
determining an onset measure of each of the oxygen saturation independent of total hemoglobin and the total hemoglobin volume fraction at an onset of the detected arrhythmia;
determining at least one later measure of each of the oxygen saturation independent of total hemoglobin and the total hemoglobin volume fraction;
determining a trend of each of the oxygen saturation independent of total hemoglobin and the total hemoglobin volume fraction in response to the onset measures and the later measures;
classifying the trends according to the state table classifications,; and
determining the cardiac rhythm status from the state table in response to the trends, wherein the state combinations include trends in the measure of oxygen saturation independent of total hemoglobin and trends in the measure of total hemoglobin volume fraction.

25. An implantable medical device, comprising:
a cardiac electrode for sensing cardiac depolarization signals;
an optical sensor configured to produce a signal corresponding to light attenuation by a volume of blood perfused tissue;
a control module coupled to the optical sensor and configured to control the light emitted by the optical sensor;
a monitoring module coupled to the optical sensor and configured to receive an optical sensor output signal and determine light attenuation for at least four spaced-apart light wavelengths; and
a processor electrically coupled to the cardiac electrode and the monitoring module and configured to receive the cardiac electrical signal, the processor being configured to:
detect an arrhythmia in response to the cardiac electrical signal,
determine an attenuation for each of the at least four wavelengths at an episode onset time point of the arrhythmia detection;
determine a second derivative of the attenuation with respect to each of two different wavelengths of the four wavelengths for the episode onset time point of the arrhythmia detection;
determine a tissue oxygen saturation independent of total hemoglobin based on a ratio of the two second derivatives determined with respect to each of the two different wavelengths for the episode onset time point;
determine a total hemoglobin volume fraction based on a selected one of the two second derivatives determined for the episode onset time point;
establish a first weighting factor applied to the tissue oxygen saturation and a second weighting factor applied to the total hemoglobin volume fraction;
determine an onset measurement at the episode onset time point based on a weighted combination of the tissue oxygen saturation and the total hemoglobin volume fraction for the time of the arrhythmia detection using the established first and second weighting factors;
compare the onset measurement to an onset detection threshold,
detect a hemodynamically unstable status of the detected arrhythmia in response to the onset measurement being less than the onset detection threshold;
determine if one of the tissue oxygen saturation and the total hemoglobin volume fraction is out of a respective acceptable range; and
adjust one of the first weighting factor and the second weighting factor used to compute the weighted combination in response to one of the tissue oxygen saturation and the total hemoglobin volume fraction being out of the respective acceptable range.

26. A method, comprising:
sensing cardiac depolarization signals;
detecting an arrhythmia in response to the depolarization signals;
controlling an optical sensor to emit light in response to the detected arrhythmia;
detecting light scattered by a volume of blood perfused tissue wherein detecting light comprises measuring an optical sensor output signal corresponding to light attenuation of at least four spaced apart light wavelengths;

computing a measure of tissue oxygenation from the optical sensor output signal, wherein computing the measure of tissue oxygenation comprises:
- computing a light attenuation for each of the at least four wavelengths;
- computing a second derivative of the light attenuation with respect to two different wavelengths;
- computing a measure of tissue oxygen saturation independent of total hemoglobin as a ratio of the second derivatives at the two different wavelengths;
- computing a measure of total hemoglobin volume fraction using the second derivative of a selected one of the two different wavelengths;
- computing the measure of tissue oxygenation as a weighted combination of the measure of oxygen saturation and the measure of total hemoglobin volume fraction;
- determining if one of the measure of oxygen saturation and the measure of total hemoglobin volume fraction is out of a respective acceptable range;
- adjusting a weighting factor used to compute the weighted combination in response to one of the measures of oxygen saturation and total hemoglobin volume fraction being out of a respective acceptable range; and
- detecting a hemodynamic status of the arrhythmia in response to the measure of tissue oxygenation.

27. The device of claim 25, further comprising a sensor coupled to the processor to sense a signal corresponding to a patient position, wherein the processor is further configured to detect the hemodynamic status in response to the measure of tissue oxygenation and the signal corresponding to the patient position.

28. The device of claim 25, further comprising a memory storing a state table relating the tissue oxygenation measurement to a cardiac status, wherein the processor is further configured to determine an absolute value of the tissue oxygenation measurement and a trended value of the tissue oxygenation measurement, and detect the hemodynamic status by determining a cardiac status stored in the state table corresponding to the absolute value and the trended value.

29. The device of claim 25, further comprising a therapy delivery module coupled to the electrode to deliver shock therapy for treating the detected arrhythmia.

\* \* \* \* \*